United States Patent
Yuan et al.

(10) Patent No.: US 7,353,117 B2
(45) Date of Patent: Apr. 1, 2008

(54) COMPUTATION OF WALL THICKNESS

(75) Inventors: Chun Yuan, Bellevue, WA (US); Chao Han, ChengDu (CN); Thomas S. Hatsukami, Mercer Island, WA (US)

(73) Assignee: University of Washington, Seattle, WA (US)

( * ) Notice: Subject to any disclaimer, the term of this patent is extended or adjusted under 35 U.S.C. 154(b) by 685 days.

(21) Appl. No.: 10/804,460

(22) Filed: Mar. 19, 2004

(65) Prior Publication Data

US 2004/0243365 A1 Dec. 2, 2004

Related U.S. Application Data

(60) Provisional application No. 60/456,680, filed on Mar. 20, 2003, provisional application No. 60/456,912, filed on Mar. 21, 2003.

(51) Int. Cl.
*G06F 19/00* (2006.01)
*G06K 9/34* (2006.01)

(52) U.S. Cl. ......................................... 702/19; 382/286
(58) Field of Classification Search .................... None
See application file for complete search history.

(56) References Cited

U.S. PATENT DOCUMENTS

| 6,443,894 | B1 | 9/2002 | Sumanaweera et al. | 600/443 |
|---|---|---|---|---|
| 2002/0193687 | A1 | 12/2002 | Vining et al. | 600/425 |
| 2004/0064029 | A1 | 4/2004 | Summers et al. | 600/407 |

OTHER PUBLICATIONS

Kang et al. (2000) Magnetic Resonance in Medicine vol. 44:968-972.*
Amenta et al. (1998) Computer Graphics: A New Voronoi-Based Surface Reconstruction Algorithm.*
Aurenhammer F. "Voronoi diagrams—A Survey of a Fundamental Geometric Data Structure." *ACM Computing Surveys* Sep. 1991; 23(5):345-405.
Bots ML, Grobbee DE. "Intima Media Thickness as a Surrogate Marker for Generalised Atherosclerosis." *Cardiovascular Drugs and Therapy.* ProQuest Medical Library. Jul. 2002: 16(4):341-351.
Buller VGM, Van der Geest RJ, Kool MD, Reiber JHC. "Accurate Three-dimensional Wall Thickness Measurement From Multi-Slice Short-Axis MR Imaging." *Computers in Cardiology.* 1995:245-248.
Dempsey RJ, Diana AL, Moore RW. "Thickness of Carotid Artery Atherosclerotic Plaque and Ischemic Risk." *Neurosurgery.* Sep. 1990; 27(3):343-348.
Ganapathy S and Dennehy TG. "A New General Triangulation Method for Planar Contours." *Computer Graphics* Jul. 1982; 16(3):69-75.

Edelsbrunner Herbert. "Geometry and Topology for Mesh Generation" © *Cambridge University Press 2001.* 1-132. <http:www.cambridge.org>.
Han C, Hatsukami TS, Hwang JN, Yuan C. "A Fast Minimal Path Active Contour Model." *IEEE Transactions on Image Processing.* Jun. 2001; 10(6):865-873.
Hubka M, Lipiecki J, Bolson EL, Martin RW, Munt B, Maza SR, Sheehan FH. "Three-dimensional echocardiographic measurement of left ventricular wall thickness: In vitro and in vivo validation." *Journal of the American Society of Echocardiograhy.* Feb. 2002;15(2):129-35.
Iannuzzi A, Wilcosky T, Mercuri M, Rubba P, Bryan FA, Bond MG. "Ultrasonographic Correlates of Carotid Atherosclerosis in Transient Ischemic Attack and Stroke." *Stroke.* ProQuest Medical Library. Apr. 1995;26(4):614-9.
Meyers D. "Multiresolution tiling." *Computer Graphics Forum* 1994; No. 5:325-340.
O'Leary DH, Polak JF, Kronmal RA, Manolio TA, Burke GL, Wolfson SK Jr. "Carotid-artery Intima and Media Thickness as a Risk Factor for Myocardial Infarction and Stroke in Older Adults." Cardiovascular Health Study Collaborative Research Group. *New England Journal of Medicine.* Jan 7, 1999;340(1):14-22.
Pignoli P, Tremoli E, Poli A, Oreste P, Paoletti R. "Intimal plus medial thickness of the arterial wall: a direct measurement with ultrasound imaging." *Circulation.* Dec. 1986;74(6):1399-406.
Schulte-Altedorneburg G, Droste DW, Felszeghy S, Kellermann M, Popa V, Hegedüs K, Hegedüs C, Schmid M, Módis L, Ringelstein EB, Csiba L. "Accuracy of In Vivo Carotid B-Mode Ultrasound Compared with Pathological Analysis: Intima-Media Thickening, Lumen Diameter, and Cross-Sectional Area." *Stroke.* Jul. 2001;32(7):1520-4.
Von Land CD, Rao SR, Reiber JHC. "Development of an Improved Centerline Wall Motion Model." *Comp Cardiol.* 1991:687-690.

\* cited by examiner

*Primary Examiner*—Lori A. Clow
(74) *Attorney, Agent, or Firm*—Ronald M. Anderson

(57) ABSTRACT

A method for automatic vessel wall thickness measurement at any point along the perimeter of either luminal or outer vessel wall boundaries. The method employs both Delaunay triangulation and multiresolution tiling. The MaxMin angle property of the Delaunay triangulation is used to define the minimum energy function to calculate thickness. Multiresolution tiling is employed to enable the MaxMin angle lemma to be determined. The triangulation MaxMin angle lemma enables a minimal energy function to be defined based on triangulation angles, providing a stable and consistent geometrical computation. Additional morphological indexes can be assessed to achieve comprehensive quantification of vascular morphology. For example, based on the wall thickness, a set of vascular shape descriptors can be developed to distinguish different types of plaque morphology at different parts of a vessel wall.

44 Claims, 12 Drawing Sheets

COMPUTATION OF WALL THICKNESS

RELATED APPLICATIONS

This application is based on two prior copending provisional applications, Ser. No. 60/456,680, filed on Mar. 20, 2003, and Ser. No. 60/456,912, filed on Mar. 21, 2003, the benefit of the filing dates of which is hereby claimed under 35 U.S.C. § 119(e).

GOVERNMENT RIGHTS

This invention was funded at least in part with grants (Nos. HL60213 and HL61851) from the National Institutes of Health, and the U.S. government may have certain rights in this invention.

FIELD OF THE INVENTION

The present invention generally relates to imaging vascular vessels, and more specifically, to determining a wall thickness of a vascular vessel from an image of the vascular vessel.

BACKGROUND OF THE INVENTION

According to the National Center for Health Statistics, cardiovascular disease is the leading cause of death in the United States. Carotid atherosclerosis is one of the main causes of stroke. Atherosclerosis is a form of arteriosclerosis characterized by the deposition of atheromatous plaques containing cholesterol and lipids on the innermost layer of the walls of large- and medium-sized arteries. Improved methods of diagnosis, treatment, and prevention of these diseases would result in a significant improvement in the quality of life of patients and a concomitant decrease in health care costs.

Traditionally, the degree to which lumen stenosis has occurred is used as a morphological marker for high risk (i.e., vulnerable) plaques. Clinical, X-ray, computerized tomography (CT), ultrasound, and magnetic resonance (MR) angiography are used to determine lumen stenosis. The determination of lumen stenosis lacks a unified approach, as evidenced by the two different methods of stenosis quantification that are most often used—the North American Symptomatic Carotid Endarterectomy Trial (NASCET) and the European Carotid Surgery Trial. Regardless of the method used, it has been demonstrated that lumen narrowing is a poor indicator of patient vulnerability to strokes. In symptomatic patients, evidence of lumen narrowing predicted only about one out of four strokes. In asymptomatic patients, evidence of lumen narrowing predicted only about one out of ten strokes. Clearly, it would be desirable to employ a more accurate predictor of a patient's risk of having a stroke using conventional imaging procedures.

Some studies indicate the importance of plaque morphological factors (in addition to stenosis) in determining thromboembolic risk. Specifically, ultrasonographic studies show that plaque thickness is a better predictor of transient ischemic attacks than vessel stenosis. Unfortunately, ultrasound measurement of plaque thickness is not highly reproducible, since such measurements produce results varying from 13.8% to 22.4%. Further evidence of the importance of plaque morphology was documented in a study by NASCET investigators showing increasing risk for stroke with ulcerated plaques, as compared to non-ulcerated plaques with similar degrees of stenosis. These results suggest that a comprehensive, quantitative analysis of plaque morphology, including lumen stenosis, wall thickness, and ulceration, will better identify vulnerable plaques.

Recent studies have shown that Magnetic Resonance Imaging (MRI) is capable of identifying plaque constituents and measuring plaque morphology. MR plaque imaging may therefore be a useful technique for characterizing plaque morphology and tissue constituents in one examination, thereby assessing both aspects of vulnerable plaque. However, current MRI techniques fail to provide the data necessary for comprehensive, quantitative analysis of plaque morphology. It would be desirable to develop methods of using MRI to obtain accurate tracing of lumen and wall boundaries, a reasonable definition of carotid wall thickness, accurate computation of lumen surface roughness, and a reasonable definition of plaque burden indexes. Techniques for tracing lumen and wall boundaries and computing lumen surface roughness have been suggested. However, a consistent and reliable technique for estimating lumen wall thickness from an image of a lumen has not been taught in the prior art.

In addition to wall thickness, other quantitative morphological parameters can be defined to assess plaque morphology. Morphological description refers to the methods that produce numeric morphological descriptors and is carried out subsequent to morphological representation. A morphological description method generates a morphological descriptor vector (also called a feature vector) from a given shape. The goal of morphological description is to uniquely characterize a shape using its morphological descriptor vector.

Previous work has established the reproducibility of in-vivo measurements of area and volume from a carotid artery MR image. These studies indicate a good agreement between in-vivo and ex-vivo measurements. Specifically, volume measurements matched to within 4%-6% and cross-sectional area measurements matched to within 5%-11% for two independent MR scans performed within 2 weeks that were reviewed by two independent reviewers. In addition, it has been determined that different contrast weighted images (T1, T2, and proton density) of comparable image quality will yield similar results in lumen and vessel wall area measurements. Such results indicate that morphological descriptors extracted from MRI may be used to characterize vascular shape variance. However, the prior art does not define a specific set of useful morphological descriptors. It would be desirable to provide vascular morphological descriptors that are based on lumen boundary, wall boundary, and wall thickness, and to use such descriptors to evaluate plaque morphology.

SUMMARY OF THE INVENTION

A first aspect of the present invention is directed to a method for determining vessel wall thickness from an image of a vessel. The method is implemented automatically with a computing device. In the method, an imaging system is coupled to the computing device and is configured to perform the wall thickness determination. The method automatically estimates vessel wall thickness at any point along the perimeter of either luminal or vessel outer wall boundaries. Both Delaunay triangulation and multiresolution tiling. Multiresolution tiling is used to determine a MaxMin angle lemma. As defined in the Delaunay triangulation, the MaxMin angle property relates a minimal energy function to triangulation angles. Thus, the determination of the MaxMin angle lemma enables the minimum energy function to calculate wall thickness. In the method, it is assumed that a single boundary cannot overlap itself.

A second aspect of the present invention is directed to a set of vascular shape descriptors that are based in part on wall thickness, which can be used to evaluate plaque morphology. 32 vascular morphological descriptors are defined as a function of lumen boundary, wall boundary, and wall thickness. The morphological descriptors include area descriptors, lumen boundary descriptors, wall boundary descriptors, wall thickness descriptors, complexity lumen-wall descriptors, and complexity thick-wall descriptors. The area descriptors define lumen area, wall area, and a ratio of wall area to lumen area. The lumen boundary descriptors, wall boundary descriptors, and wall thickness descriptors demonstrate shape variance, while the complexity lumen-wall descriptors and complexity thick-wall descriptors demonstrate relative variance. The descriptors can be used to automate the clinical plaque analysis.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 1 schematically illustrates edge flipping, used with Delaunay triangulation in the present invention for determining the thickness of a lumen wall from an image of the lumen;

FIGS. 2A-2E schematically illustrate multiresolution tiling, which is used in the present invention;

Figure 6:
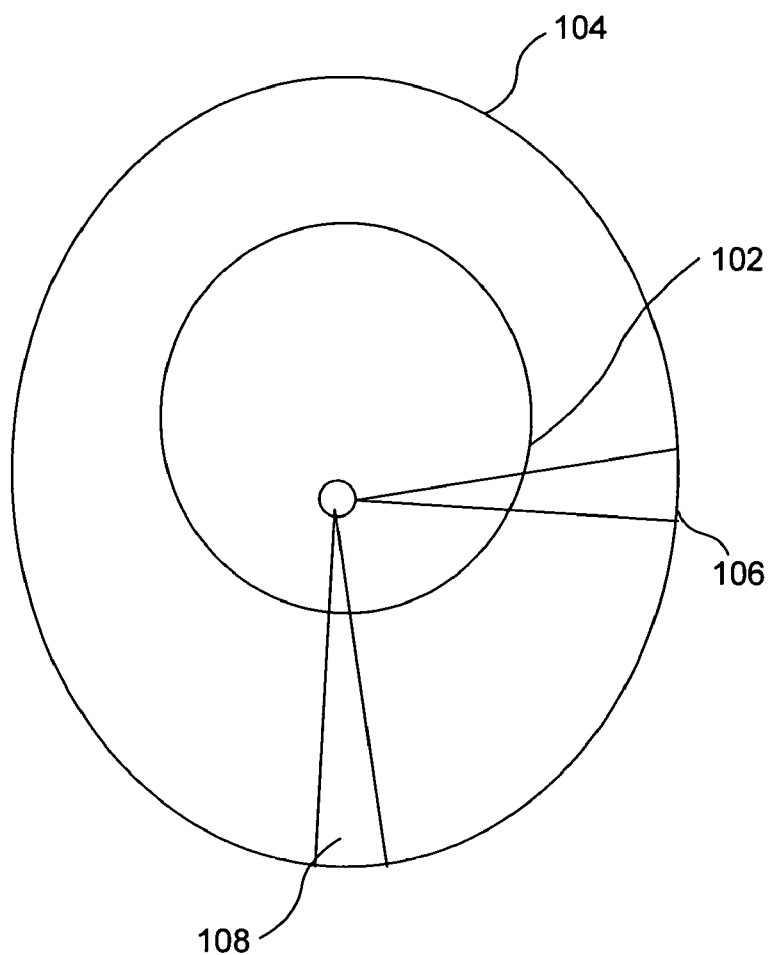
Figure 7A:
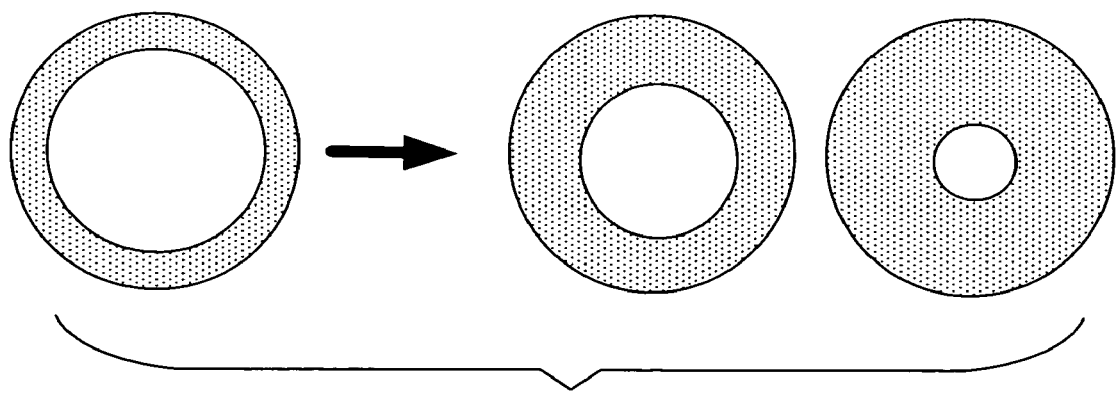
Figure 7B:
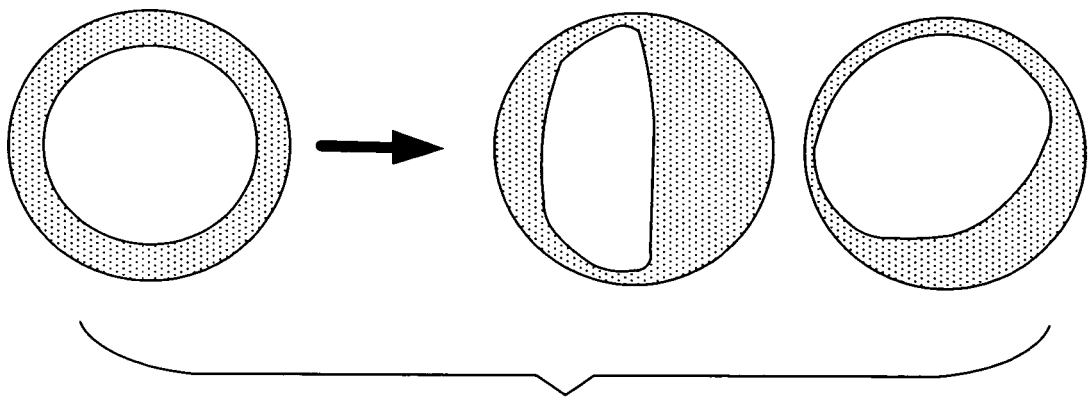
Figure 7C:
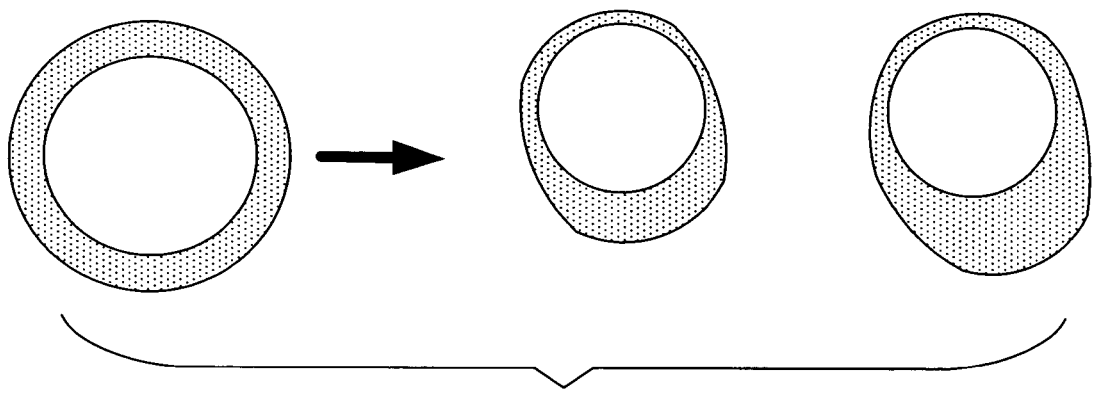
Figure 7D:
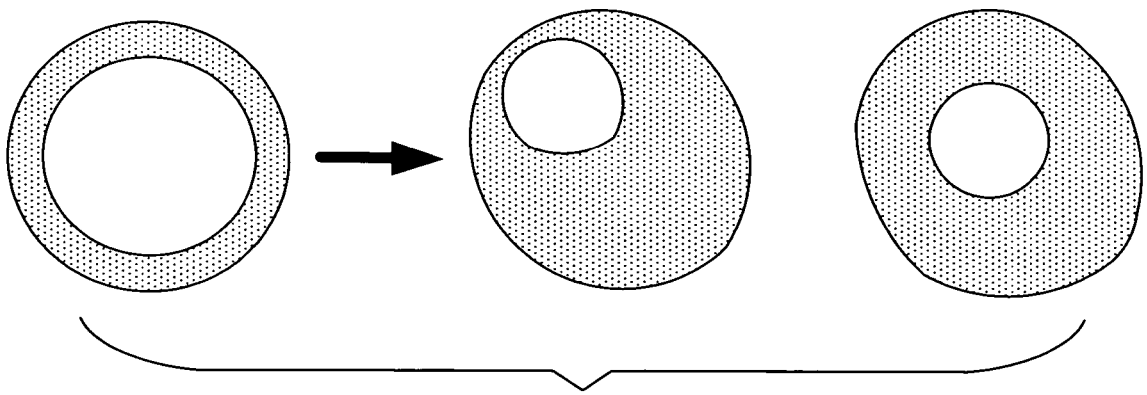
Figure 8A:
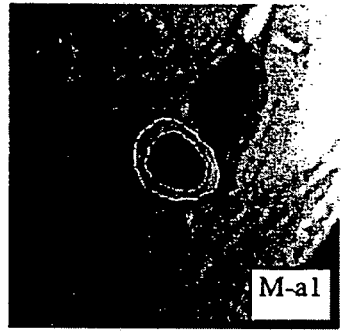
Figure 8A:
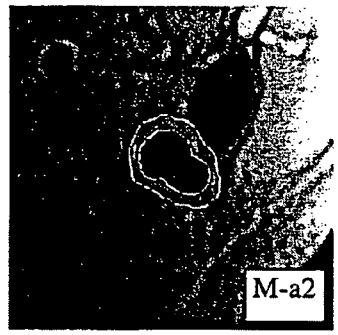
Figure 8A:
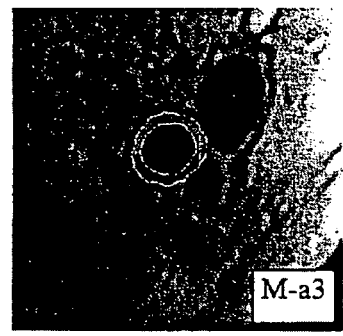
Figure 8A:
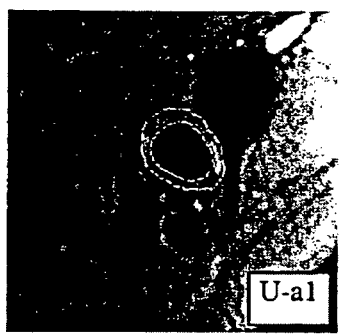
Figure 8A:
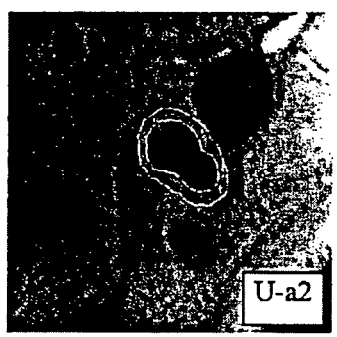
Figure 8A:
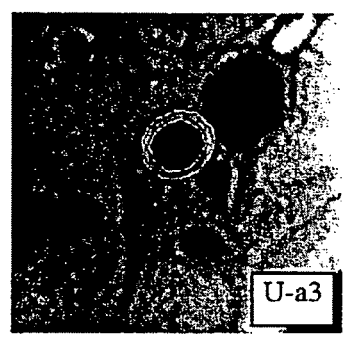
Figure 8A:
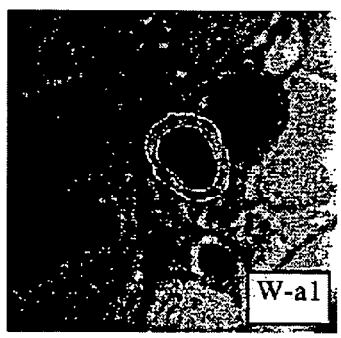
Figure 8A:
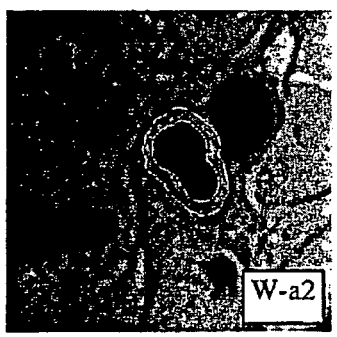
Figure 8A:
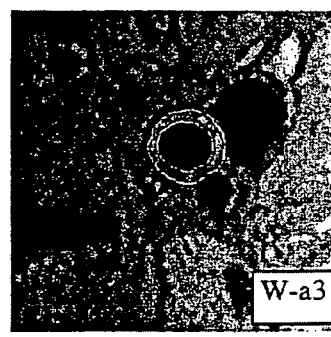
Figure 8B:
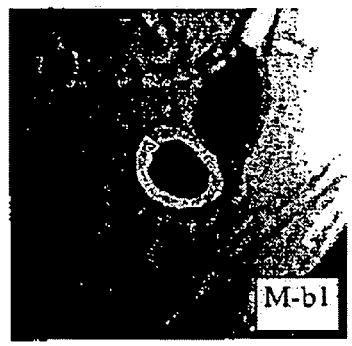
Figure 8B:
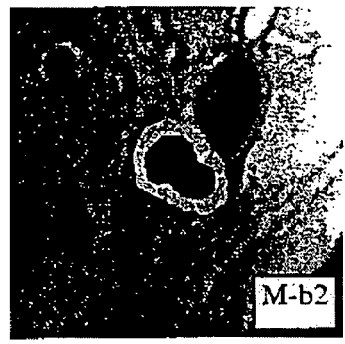
Figure 8B:
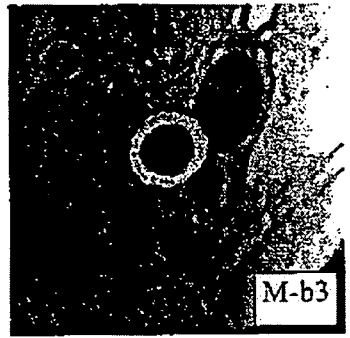
Figure 8B:
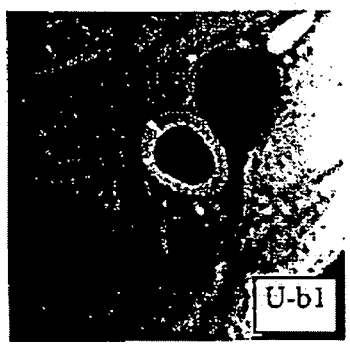
Figure 8B:
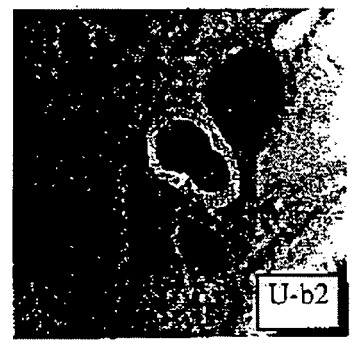
Figure 8B:
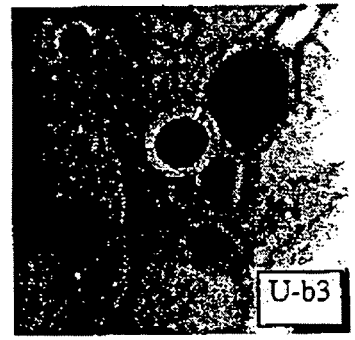
Figure 8B:
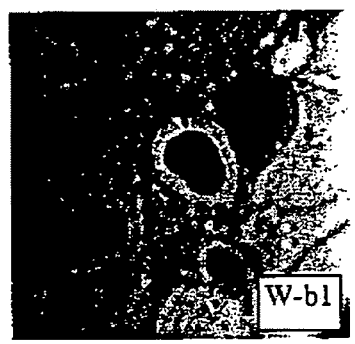
Figure 8B:
Figure 8B:
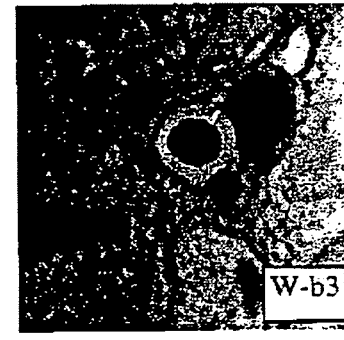
Figure 9A:
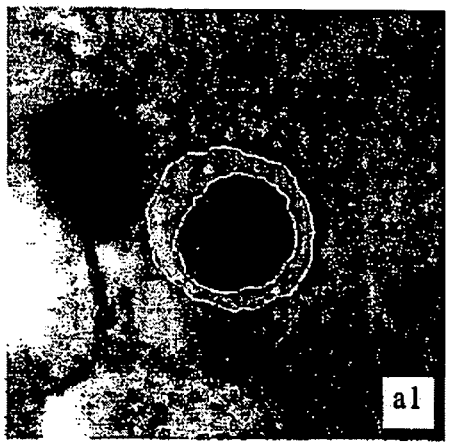
Figure 9A:
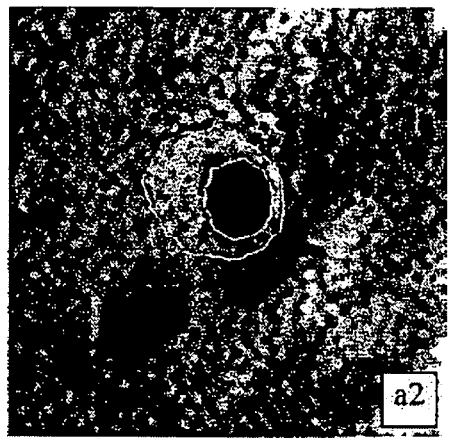
Figure 9A:
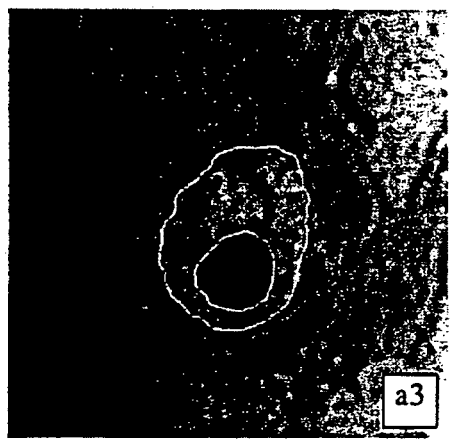
Figure 9A:
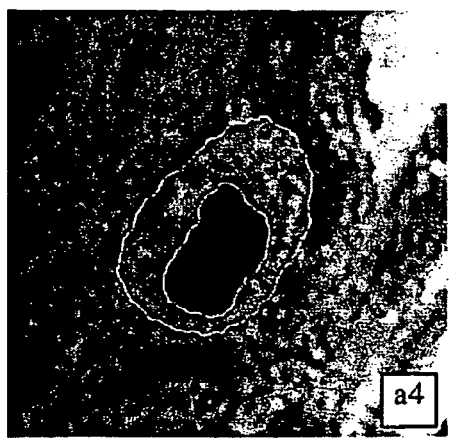
Figure 9B:
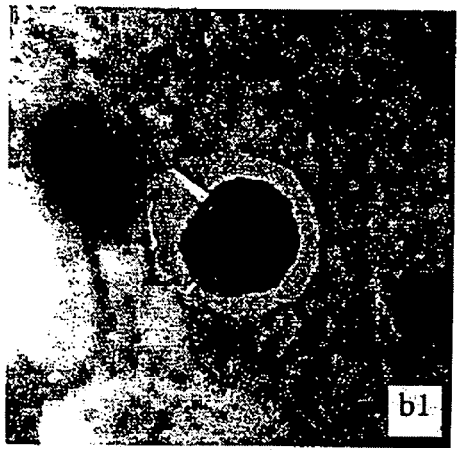
Figure 9B:
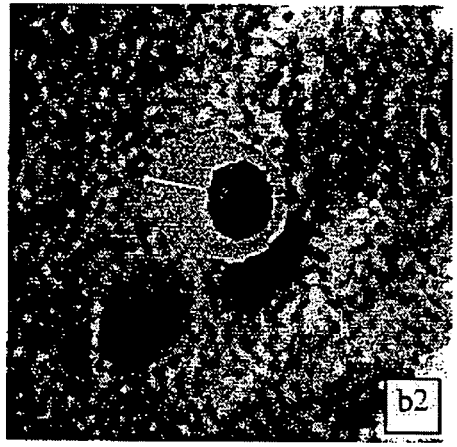
Figure 9B:
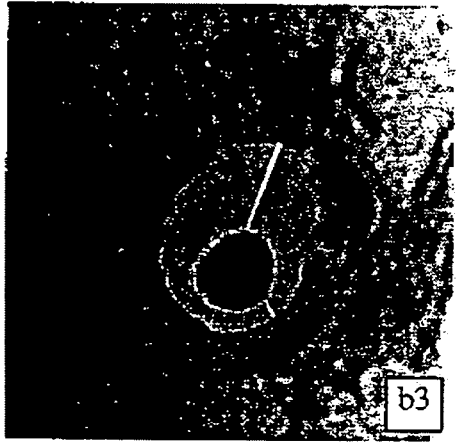
Figure 9B:
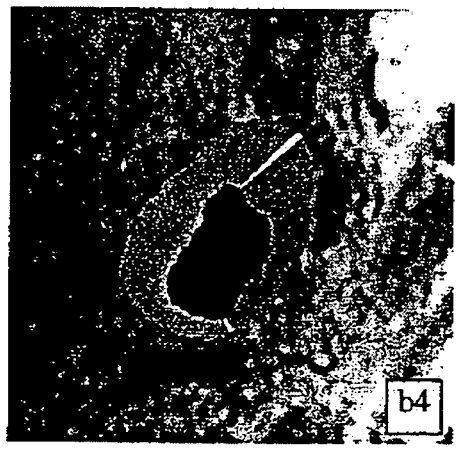
Figure 10:
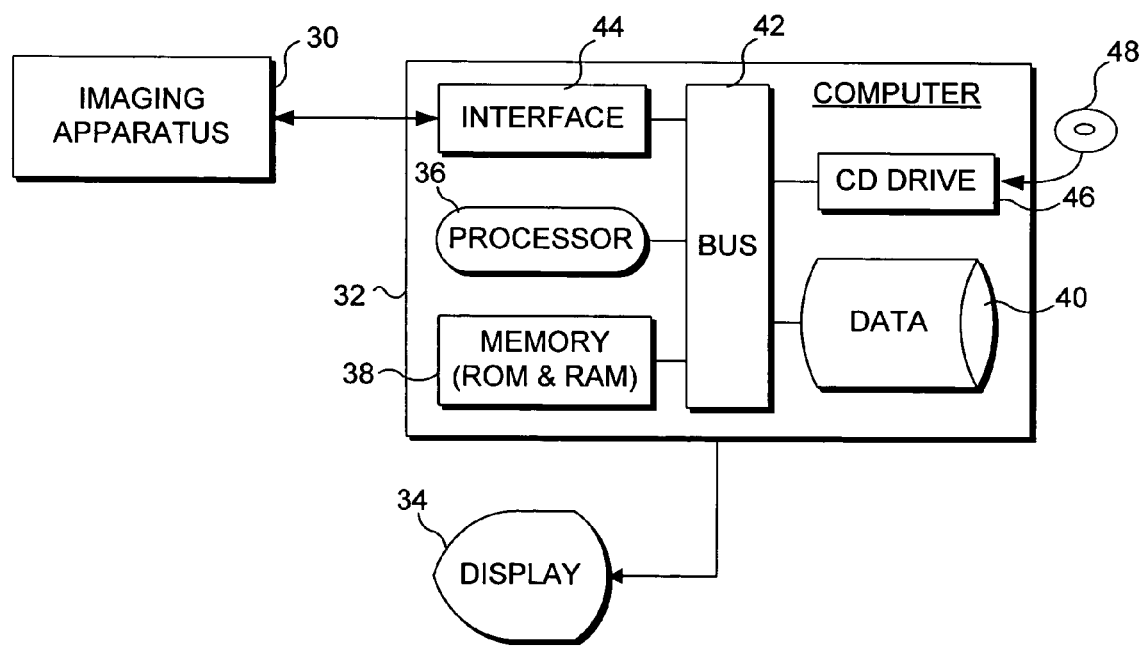

FIG. 6 schematically illustrates the outer wall boundary and the lumen boundary, which with the wall thickness value, are employed to define a plurality of morphological descriptors used to evaluate plaque morphology, in accord with a second aspect of the present invention;

FIG. 7A schematically illustrates stenosis of a lumen, wherein the lumen and wall areas change without a change in the lumen shape;

FIG. 7B schematically illustrates stenosis of a lumen, wherein the lumen boundary changes shape, but the outer wall boundary does not;

FIG. 7C schematically illustrates a lumen, wherein the lumen boundary does not change changes shape, but the outer wall boundary does;

FIG. 7D schematically illustrates stenosis of a lumen, wherein there is variance in the lumen boundary and the outer wall boundary;

FIG. 8A are exemplary images of a patient's carotid artery obtained at three different facilities, showing extracted contours;

FIG. 8B are exemplary images of a patient's carotid artery obtained at three different facilities, showing minimum and maximum wall thicknesses;

FIG. 9A are exemplary images of different patients' carotid arteries, illustrating extracted contours;

FIG. 9B are exemplary images of different patients' carotid arteries, again showing minimum and maximum wall thicknesses; and FIG. 10 is a block diagram of a computer system suitable for implementing the present invention.

DESCRIPTION OF THE PREFERRED EMBODIMENT

The present invention is directed to calculating the wall thickness of a lumen from an image of the lumen. In this invention, a set of 32 vascular shape descriptors, which are based in part on wall thickness, can be used to evaluate plaque morphology. The method of calculating wall thickness and the set of vascular descriptors can be combined to enable automated clinical plaque analysis to be achieved.

The method for estimating wall thickness employs both Delaunay triangulation and multiresolution tiling. In a particularly preferred implementation, the lumen is a blood vessel, and the wall thickness of the blood vessel determined by the method can be used as a predictor of whether the patient is at risk of a stroke.

Delaunay triangulation is widely used for unstructured mesh generation in computer graphics and is suitable for many applications. The present invention utilizes one of the Delaunay triangulation properties, the MaxMin angle property, to define a minimum energy function, which is then used to calculate wall thickness. Using Delaunay triangulation enables consistent and stable results to be achieved. Multiresolution tiling is then employed to determine the MaxMin angle.

The MaxMin Angle Lemma is as follows. Among all triangulations of a finite set $s \subseteq \Re^2$, the Delaunay triangulation maximizes the minimum angle. This Lemma implies that the smallest angle in any triangulation is no larger than the smallest angle in the Delaunay triangulation.

Figure 1:
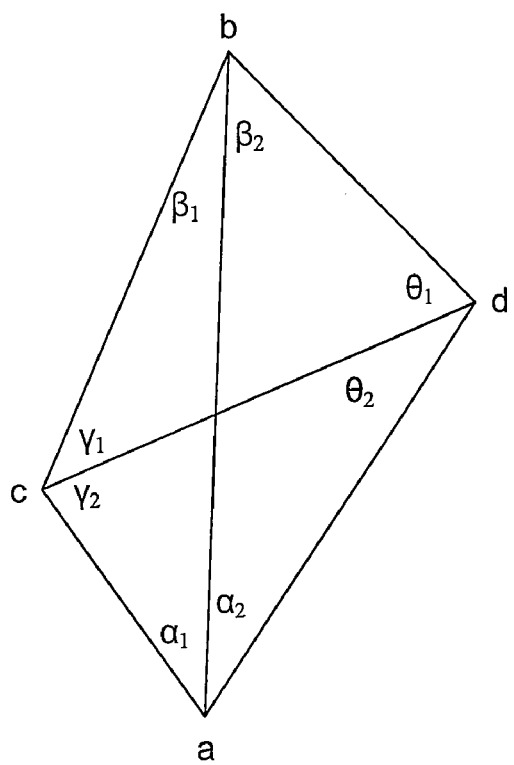

An elementary operation of Delaunay triangulation is edge flipping. An edge flip substitutes two new triangles for two old triangles, but does not decrease the smallest angle in the triangles. Edge flipping can be used to change angles, as is shown in FIG. 1. In FIG. 1, edge ab is flipped to edge cd. The old angles are $\alpha_1$, $\beta_1$, $\gamma_1+\gamma_2$, $\alpha_2$, $\beta_2$, and $\theta_1+\theta_2$, and the new angles achieved by edge flipping are $\gamma_1$, $\theta_1$, $\beta_1+\beta_2$, $\gamma_2$, $\theta_2$, and $\alpha_1+\alpha_2$. A minimal energy function to compute thickness based on maximizing the minimum angle in a set of triangulations $S \subseteq \Re^2$ is defined as follows:

$$\text{Min}\left(\frac{1}{\sum_{i=1}^{N} \theta_i}\right) \quad (0)$$

where $\theta_1$ is the minimum angle in a triangle i, and N is the number of triangulations in $S \subseteq \Re^2$. Thus, thickness can be calculated by minimizing the energy function (i.e., using Equation 0, above).

Figure 2A:
Figure 2A:
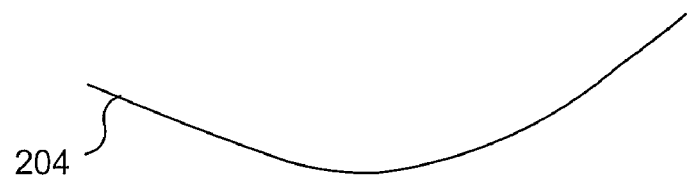
Figure 2B:
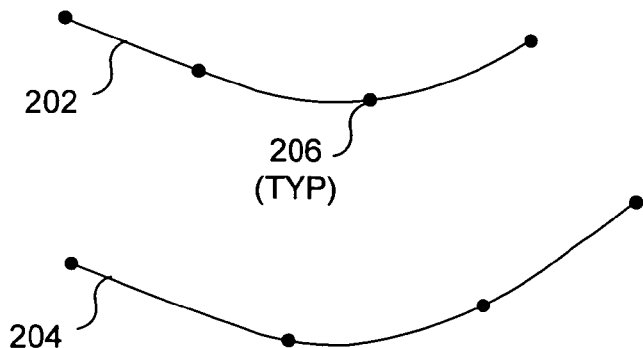
Figure 2C:
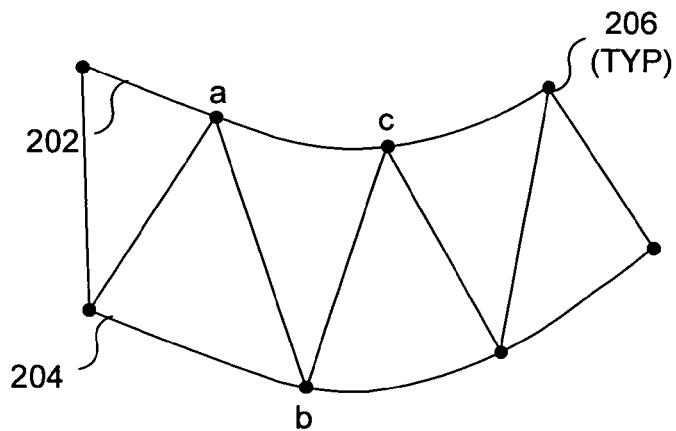
Figure 2D:
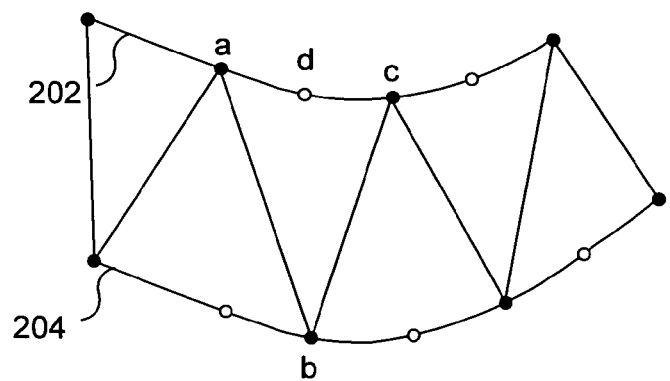
Figure 2E:
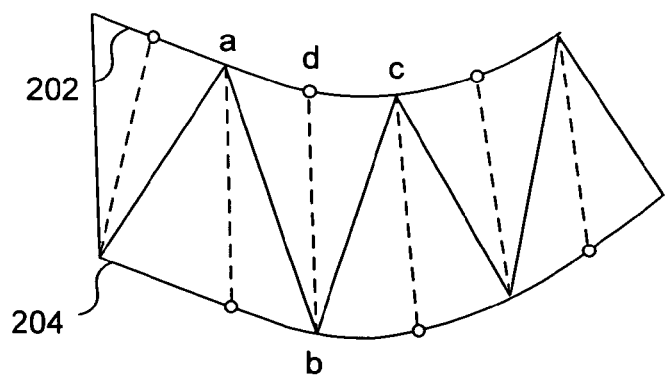

A key aspect of the present invention is to use tiling optimization to determine the smallest angle in a triangulation. Tiling optimization is described below, in connection with FIG. 2A-2E. Tiling optimization involves inserting new vertices and edges from the lower resolution level. Referring to FIG. 2E, vertex d is inserted into triangle abc in the lower resolution level, yielding quadrilateral abcd. The inserted edge bd splits quadrilateral abcd into triangles abd and dbc.

In FIG. 2E, new vertices are indicated by circles, and inserted edges are indicated by dashed lines. Note triangles abd and dbc match the curve of the lumen more closely than triangle abc does, thus inserting the vertex d and edge bd increases the resolution.

Now assume line ab is a "suspect" edge. Line ab belongs to two triangles, abc and abd. The union of those two triangles is a convex quadrangle, abcd. Thus, ab and cd can be flipped. Formally, this means that line ab, triangle abc and triangle abd are removed from the triangulation and new line cd, new triangle acd and new triangle bcd are added to the triangulation (FIG. 1 shows such a flipping operation). Schematically, the result of edge flipping resembles a tetrahedron with the front and back superimposed. Such edge flipping is an elementary operation to convert an arbitrary triangulation to the Delaunay triangulation. In the present invention, a stack is used to maintain an invariant, so that unless an edge is locally Delaunay, it resides on the stack. Initially, all "suspect" edges are pushed on the stack, and the following operation is performed for each edge:

```
WHILE stack is non-empty DO
    POP ab from stack and unlabel it;
    IF ab not locally Delaunay then flip ab to cd;
    FOR xy ∈ {ac,bd} do
        IF xy unlabeled then
            label xy and push it on stack
        END IF
    ENDFOR
END IF
END WHILE
```

Multiresolution analysis enables the tiling problem to be optimized. A first step is to reduce the size of the problem by using multiresolution analysis to find low-resolution approximations to the original contours. Detail is then added to the low-resolution tiling by inserting edges at newly added vertices, and improving the tiling by local edge flipping under the control of the minimal energy function. The specific steps involved in multiresolution tiling are as follows:

1. Decompose each contour into a set of low-resolution versions based on wavelet analysis as disclosed by M. David, "Multiresolution Tiling," Computer Graphics Form, vol. 13, no. 5, pp. 325-340, 1994. FIG. 2A schematically illustrates a contour 202 and a contour 204. In the context of a vascular vessel, contour 202 corresponds to a lumen boundary, while contour 204 corresponds to an outer wall boundary. FIG. 2B schematically illustrates contour 202 and contour 204 being decomposed into a low resolution set of individual points 206.

2. Compute tiling for the low-resolution contours using the "greedy" method described by S. Ganapathy and T. Dennehy in "A new triangulation method for planar contours," Computer Graphics, vol. 16, pp. 69-75, 1982. FIG. 2C schematically illustrates the triangulation of points 206 in each low resolution set.

3. Label all cross edges as "suspect" edges and put them into a stack. Edges ab and bc are cross edges, in that such edges couple points on each contour (see FIG. 2C).

4. Optimize the tiling by flipping the local edge under control of the minimal energy function.

5. Insert a new vertex on both contours at triangle edge of the tiling from the lower resolution level, so that the former triangles are now quadrilaterals. FIG. 2D schematically illustrates the insertion of additional vertices, such as vertex d. Triangle abc is now quadrilateral abcd.

6. Construct an edge from the inserted vertex to the quadrilateral vertex on the other contour, splitting the quadrilateral into two triangles, as shown in FIG. 2E (see edge bd).

7. Label each old cross edge as a "suspect" edge and put them into a stack.

8. Optimize the tiling by flipping the local edge under control of the minimal energy function.

9. Repeat steps 5-9 until the original resolution (or a desired resolution) is reached.

To validate the performance of the thickness estimation, two experiments were designed. A first experiment estimated the thickness of carotid phantom MR images (image size=256×256; pixel size=10.32 mm; slice thickness=2.0 mm; number of slices=6). A second experiment applied the thickness estimation to carotid MR images (image size=256×256; pixel size=10.25 mm; slice thickness=2.0 mm; number of slices=30) of a patient. The phantom MR images were used to test the consistency of thickness method. The patient's carotid MR images were used to show that the thickness can readily characterize different vascular morphological types.

Figure 3:
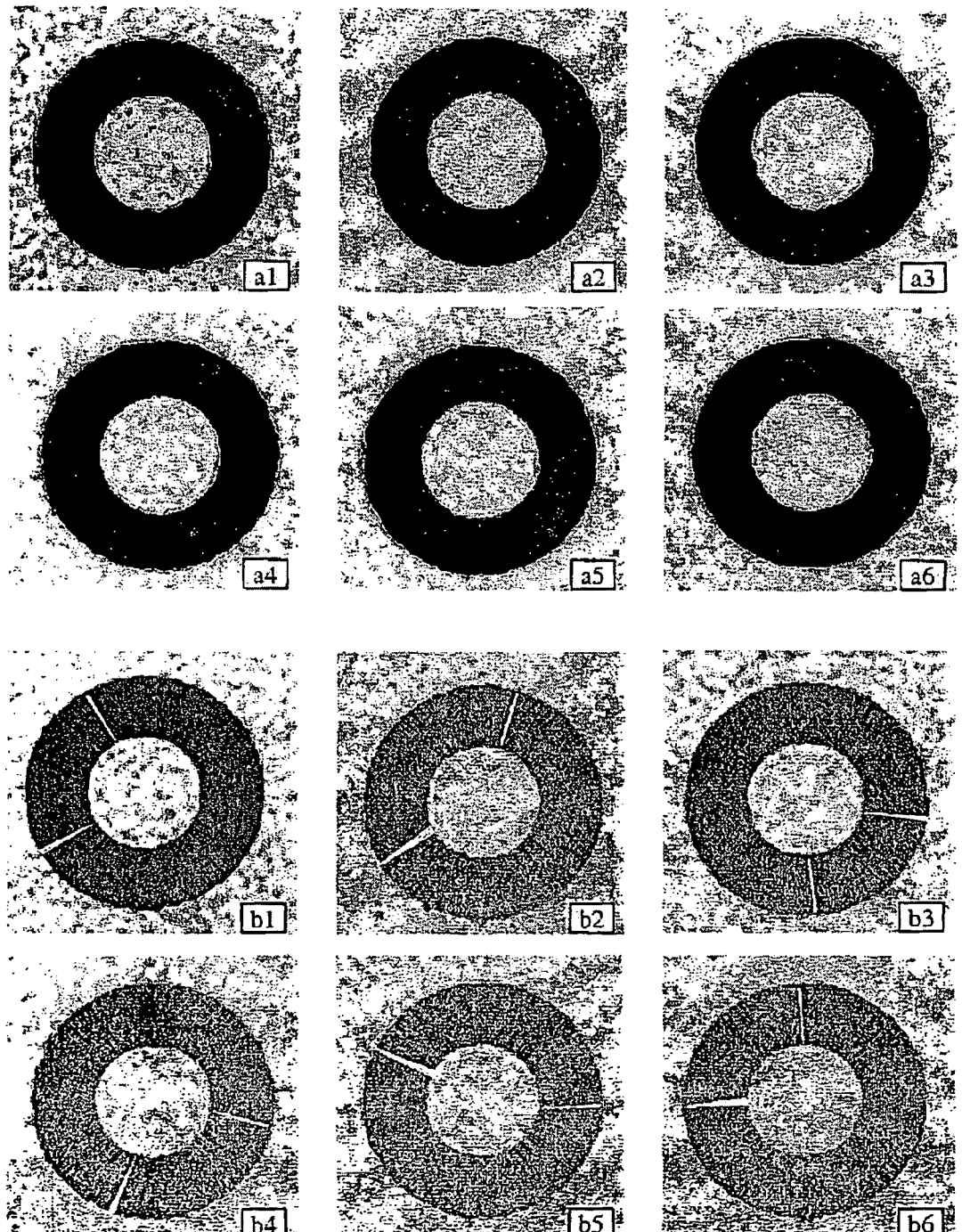
FIG. 3 is a visual representation of a wall thickness estimation in accord with the present invention, as applied to carotid phantom MR images.

FIG. 3 is a visual representation of results obtained in the first experiment, where wall thicknesses of carotid phantom MR images were estimated. Portions a1-a6 of FIG. 3 correspond to original images with extracted contours, whereas portions b1-b6 correspond to estimated thickness. The bright lines in portions b1-b6 indicate the maximum and minimum thicknesses. Table 1 summarizes a few of the morphological indexes calculated from thicknesses estimated on the phantom images of FIG. 3. The morphological indexes include thickness mean, thickness standard deviation, minimum thickness, maximum thickness, ratio of minimum thickness to maximum thickness (Min/Max), and the ratio of thickness standard deviation to thickness mean (Dev/Mean). Because the morphology should not change much in a short segment of common artery of the carotid phantom, the standard deviation of mean thickness, minimum thickness, and maximum thickness should be very small. Table 1 shows that the ratio of the standard deviation to each of the average of mean thickness, the average of minimum thickness, and the average of maximum thickness is 0.55%, 1.54%, and 0.85%, respectively. These results indicate that the thickness measurement method of the present invention is stable and consistent.

TABLE 1

Morphological indexes calculated on the phantom images (mm)

| Image No | Mean | Deviation | Min Thick | Max Thick | Min/Max | Dev/Mean |
|---|---|---|---|---|---|---|
| 1 | 4.142 | 0.098 | 3.874 | 4.394 | 0.882 | 0.024 |
| 2 | 4.119 | 0.111 | 3.788 | 4.339 | 0.873 | 0.027 |
| 3 | 4.134 | 0.091 | 3.945 | 4.393 | 0.898 | 0.022 |
| 4 | 4.148 | 0.085 | 3.935 | 4.380 | 0.898 | 0.020 |
| 5 | 4.183 | 0.100 | 3.941 | 4.452 | 0.885 | 0.024 |
| 6 | 4.166 | 0.081 | 3.895 | 4.368 | 0.892 | 0.019 |
| Average | 4.149 | 0.094 | 3.896 | 4.388 | 0.888 | 0.023 |
| Deviation | 0.023 | 0.011 | 0.060 | 0.037 | 0.010 | 0.003 |
| Dev/Average | 0.55% | | 1.54% | 0.85% | 1.12% | |

Figure 4:
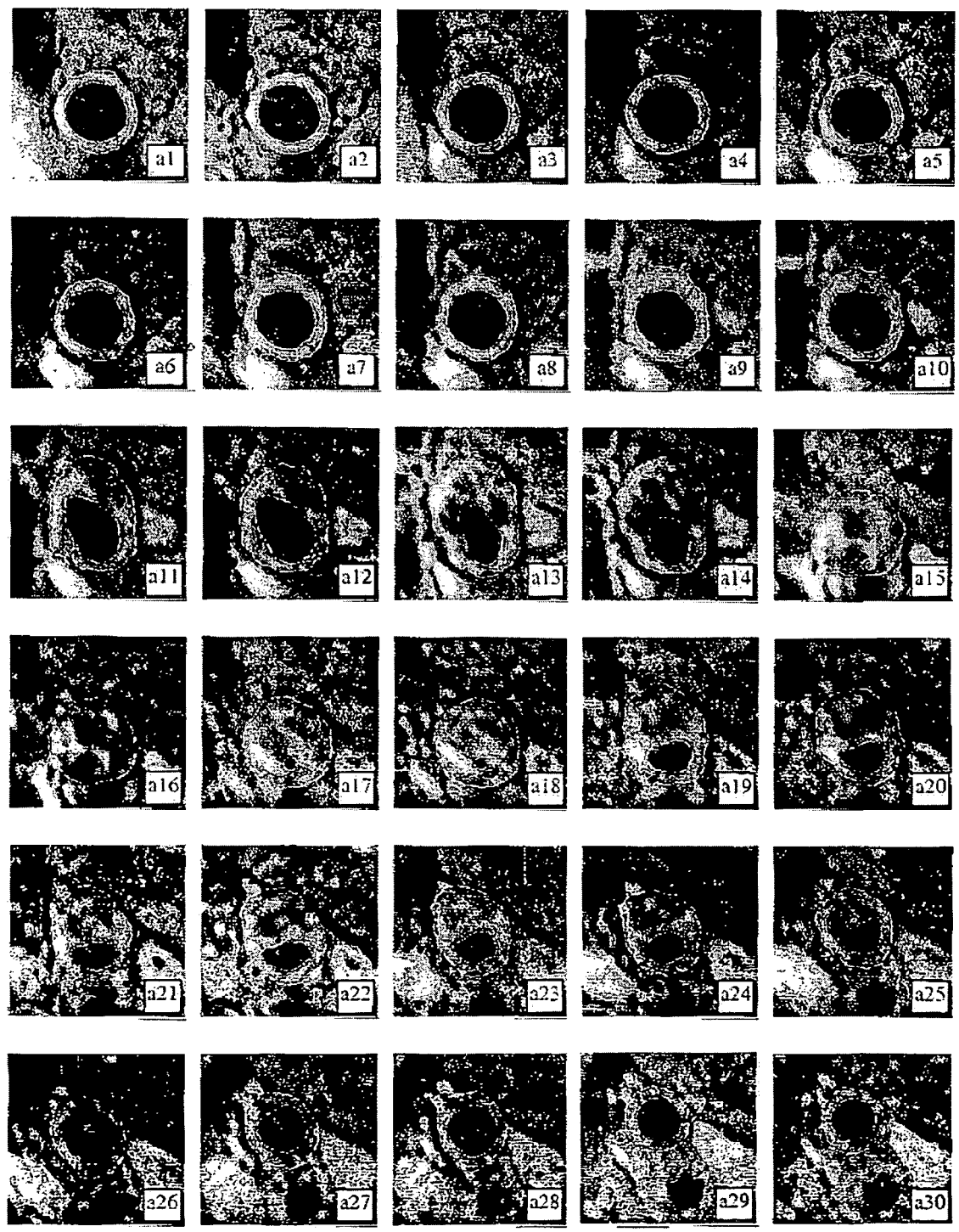
FIG. 4 are exemplary patient carotid MR images.
Figure 5:
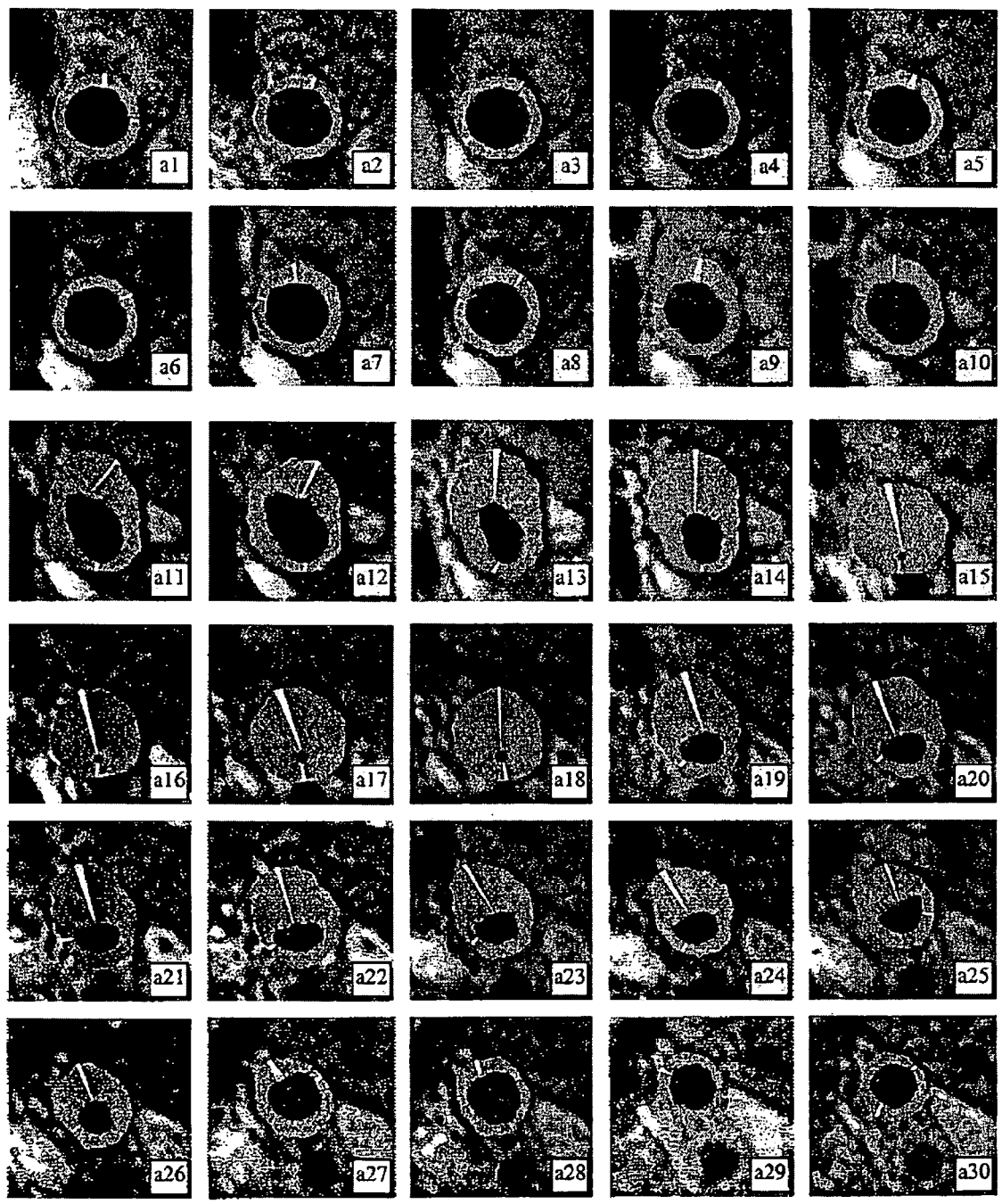
FIG. 5 is a visual representation of wall thickness estimation, as applied to the patient carotid MR images of FIG. 4, in accord with the present invention.

FIGS. 4 and 5 are provided to illustrate the results obtained in the second experiment, where wall thicknesses of a patient's carotid MR images were estimated. For example, image a14 shows the bifurcation of the common carotid artery. FIG. 4 includes original images, with extracted contours, while FIG. 5 indicates the estimated thicknesses with bright lines corresponding to maximum and minimum thicknesses.

Table 2 summarizes a few of morphological indexes calculated from thicknesses based on patient's images in FIG. 5, which include thickness mean, thickness standard deviation, minimum thickness, maximum thickness, ratio of minimum thickness to maximum thickness (Min/Max), and ratio of thickness standard deviation to thickness mean (Dev/Mean).

TABLE 2

Morphological indexes calculated on patient images in FIG. 5

| Image | Bifurcation | Mean | Deviation | MinThick | MaxThick | Min/Max | Dev/Mean |
|---|---|---|---|---|---|---|---|
| 1 | −13 | 0.91 | 0.12 | 0.73 | 1.18 | 0.62 | 0.13 |
| 2 | −12 | 0.85 | 0.10 | 0.61 | 1.12 | 0.55 | 0.12 |
| 3 | −11 | 0.88 | 0.08 | 0.69 | 1.09 | 0.64 | 0.09 |
| 4 | −10 | 0.83 | 0.07 | 0.65 | 1.01 | 0.64 | 0.08 |
| 5 | −9 | 0.93 | 0.15 | 0.60 | 1.23 | 0.49 | 0.16 |
| 6 | −8 | 0.84 | 0.12 | 0.51 | 1.09 | 0.47 | 0.14 |
| 7 | −7 | 1.07 | 0.24 | 0.67 | 1.67 | 0.40 | 0.23 |
| 8 | −6 | 0.98 | 0.17 | 0.66 | 1.27 | 0.52 | 0.18 |
| 9 | −5 | 1.25 | 0.41 | 0.76 | 2.13 | 0.36 | 0.33 |
| 10 | −4 | 1.17 | 0.40 | 0.64 | 2.10 | 0.30 | 0.34 |
| 11 | −3 | 1.94 | 0.94 | 0.69 | 3.91 | 0.18 | 0.48 |
| 12 | −2 | 1.72 | 0.83 | 0.74 | 3.57 | 0.21 | 0.48 |
| 13 | −1 | 2.49 | 1.14 | 1.04 | 4.65 | 0.22 | 0.46 |
| 14 | 0 | 2.72 | 1.64 | 0.57 | 5.69 | 0.10 | 0.60 |
| 15 | 1 | 3.98 | 1.67 | 1.11 | 6.19 | 0.18 | 0.42 |
| 16 | 2 | 3.79 | 1.56 | 1.20 | 5.99 | 0.20 | 0.41 |
| 17 | 3 | 3.71 | 1.37 | 1.54 | 5.83 | 0.26 | 0.37 |
| 18 | 4 | 3.62 | 1.29 | 1.67 | 5.64 | 0.30 | 0.36 |
| 19 | 5 | 2.58 | 1.64 | 0.60 | 5.65 | 0.11 | 0.64 |
| 20 | 6 | 2.62 | 1.57 | 0.79 | 5.28 | 0.15 | 0.60 |
| 21 | 7 | 2.60 | 1.58 | 0.98 | 5.48 | 0.18 | 0.61 |
| 22 | 8 | 2.57 | 1.58 | 0.66 | 5.31 | 0.12 | 0.62 |
| 23 | 9 | 2.37 | 1.39 | 0.85 | 5.06 | 0.17 | 0.59 |
| 24 | 10 | 2.22 | 1.30 | 0.75 | 4.53 | 0.17 | 0.59 |
| 25 | 11 | 1.82 | 0.94 | 0.92 | 3.57 | 0.26 | 0.52 |
| 26 | 12 | 2.03 | 0.83 | 0.92 | 3.50 | 0.26 | 0.41 |
| 27 | 13 | 1.21 | 0.35 | 0.62 | 2.00 | 0.31 | 0.29 |
| 28 | 14 | 0.97 | 0.26 | 0.54 | 1.53 | 0.35 | 0.27 |
| 29 | 15 | 0.87 | 0.20 | 0.39 | 1.19 | 0.33 | 0.22 |
| 30 | 16 | 0.93 | 0.19 | 0.54 | 1.28 | 0.42 | 0.20 |

Table 2 shows that different wall shapes can be readily separated into different categories based on morphological indexes. For example, if Min/Max is employed as an index to separate the portions shown in FIG. 5 into different categories, and the threshold for Min/Max is set to 0.3, images a1-a9 fall in a first group, images a10-a26 fall in a second group, and images a27-a30 fall into a third group.

As noted above, the present invention is also includes a set of 32 vascular morphological descriptors, which are defined based on measurements of lumen boundary, wall boundary, and wall thickness. Techniques for boundary tracing are known in the art (see Han, C. et al. 2001. "A fast minimal path active contour model." *IEEE Transactions on Image Processing,* 10(6):865-873, the disclosure and Figures of which are hereby specifically incorporated herein by reference). Determination of wall thickness based on using Delaunay triangulation and multiresolution tiling is discussed in detail above. The morphological description includes area descriptors, simple descriptors, and complexity descriptors.

The area descriptors show lumen area, wall area, and their relative position and ratio. The simple descriptors include lumen boundary descriptors, wall boundary descriptors, and wall thickness descriptors. The complexity descriptors include complexity lumen-wall descriptors, and complexity thick-wall descriptors. The simple descriptors demonstrate shape variance, while the complexity descriptors demonstrate relative variance between lumen boundary, outer boundary, and wall thickness. The reproducibility of the descriptors has been tested on MR images obtained from both normal and diseased human carotid arteries.

The formulation for the morphological descriptors will first be discussed, followed by specific definitions of the descriptors for vascular morphological analysis. Finally, empirical data supporting the present invention will be discussed.

FIG. 6 schematically illustrates an outer wall boundary 104 and a lumen boundary 102 that are used in connection with the wall thickness value to define the morphological descriptors. A maximum radii 108 and a minimum radii 106 can then be computed, as discussed in detail below.

In regard to the formulation of the morphological descriptors of the present invention, suppose that a contour has N vertices and the edges connect the vertices in the following order: $[(x_1, y_1), (x_2, y_2), \ldots, (x_N, y_N)]$, with the last vertex being connected to the first vertex. The area of a contour is defined as:

$$\text{Area} = \text{abs}\left(\frac{1}{2}\sum_{i=1}^{N} x_i y_{i\oplus 1} - x_{i\oplus 1} y_i\right) * p_x * p_y \qquad (1)$$

where $i \oplus 1$ is $(i+1)$ mod N, and $P_x$, $p_y$ are the edge size of rectangular pixel.

A radius of a contour is defined as a distance from the centroid to a point on the contour. The centroid of a contour is defined as:

$$\text{Centroid}(x, y) = \{\text{Centroid}(x), \text{Centroid}(y)\} = \left\{\frac{1}{N}\sum_{i=1}^{N} x_i, \frac{1}{N}\sum_{i=1}^{N} y_i\right\} \quad (2)$$

A radius i of a contour is defined as:

$$\text{Radius}(i) = \text{sqrt}((x_i - \text{Centroid}(x))^2 \ast p_x^2 + (y_i - \text{Centroid}(y))^2 \ast p_y^2) \quad (3)$$

The minimum radii and the maximum radii of a contour are defined as:

$$\text{MinRadii} = \frac{1}{2\delta} \sum_{i=l_{\min}-\delta}^{l_{\min}+\delta} \text{Radius}(i) \quad (4)$$

$$\text{MaxRadii} = \frac{1}{2\delta} \sum_{i=l_{\max}-\delta}^{l_{\max}+\delta} \text{Radius}(i) \quad (5)$$

where $\delta$ is a neighborhood around a minimum radius location $l_{min}$, and the maximum radius location $l_{max}$:

$$l_{\min} = \underset{i=1,2\cdots N}{\text{argmin}}(\text{Radius}(i)) \quad (6)$$

$$l_{\max} = \underset{i=1,2\cdots N}{\text{argmax}}(\text{Radius}(i)) \quad (7)$$

The mean and standard deviation of the radii of a contour are defined as:

$$\text{MeanRadii} = \frac{1}{N}\sum_{i=1}^{N} \text{Radius}(i) \quad (8)$$

$$\text{SDRadii} = \sqrt{\frac{1}{N}\sum_{i=1}^{N}(\text{Radius}(i) - \text{MeanRadii})^2} \quad (9)$$

Similarly, suppose that wall thicknesses of number M are being evaluated. The minimum of all wall thicknesses, the maximum of all wall thicknesses, the mean of all wall thicknesses, and standard deviation of all wall thicknesses are defined as:

$$\text{MinThick} = \frac{1}{2\delta} \sum_{j=l_{\min}-\delta}^{l_{\min}+\delta} \text{Thickness}(i) \quad (10)$$

$$\text{MaxThick} = \frac{1}{2\delta} \sum_{j=l_{\max}-\delta}^{l_{\max}+\delta} \text{Thickness}(i) \quad (11)$$

$$\text{MeanThick} = \frac{1}{M}\sum_{i=1}^{M} \text{Thickness}(i) \quad (12)$$

$$\text{SDThick} = \sqrt{\frac{1}{N}\sum_{i=1}^{M}(\text{Thickness}(i) - \text{MeanThick})^2} \quad (13)$$

where $\delta$ is the neighborhood around the minimum thickness location, $l_{min}$, and maximum thickness location, $l_{max}$, defined as:

$$l_{\min} = \underset{i=1,2,\cdots,M}{\text{argmin}}(\text{Thickness}(i)) \quad (14)$$

$$l_{\max} = \underset{i=1,2,\cdots,M}{\text{argmax}}(\text{Thickness}(i)) \quad (15)$$

The specific definitions of the area descriptors, the simple descriptors, and the complexity descriptors of the present invention will now be provided. Area descriptors include lumen area (LumenArea), outer-wall boundary area (OuterArea), wall area (WallArea), and the ratio of the lumen area to the outer-wall boundary area (LORatio). The lumen area and outer-wall boundary area are calculated from Equation (1). The wall area and the ratio are computed from:

$$\text{WallArea} = \text{OuterArea} - \text{LumenArea} \quad (16)$$

$$\text{LORatio} = (\text{LumenArea}/\text{OuterArea}) \ast 100\% \quad (17)$$

The LumenArea, OuterArea, and WallArea specify the physical area size of the artery, and the LORatio indicate the LumenArea as a percentage of OuterArea. These area descriptors represent the stenosis and variation along a vessel, as schematically shown in FIGS. 7A-7D. In FIG. 7A the lumen and wall areas change without shape variance.

The simple descriptors are based on one dimensional distance, e.g., one of lumen radii, outer-wall boundary radii, and wall thickness. The simple descriptors include lumen boundary descriptors, outer-wall boundary descriptors, and wall thickness descriptors. Each simple descriptor group includes the mean, the minimum, the maximum, the ratio of the minimum to the maximum, the ratio of minimum to the mean, the ratio of the mean to the maximum, and the ratio of the standard deviation to the mean of a feature parameter. The mean descriptor, the minimum descriptor, and the maximum descriptor demonstrate the physical radii size or thickness size, and the ratio descriptors show the relationship among the mean descriptor, the minimum descriptor, and the maximum descriptor. The lumen boundary descriptors, wall boundary descriptors, and wall thickness descriptors indicate shape variance.

FIG. 7B schematically illustrates lumen boundary shape variance without outer wall boundary variance. FIG. 7C schematically illustrates outer wall boundary shape variance without lumen area variance. FIG. 7D schematically illustrates lumen boundary and outer wall boundary variance. Thus, it will be evident that the descriptors provide detail relating to vessel morphology.

The mean of the lumen boundary radii (MeanLRadii), the minimum of the lumen boundary radii (MinLRadii), and the maximum of the lumen boundary radii (MaxLRadii) are computed from Equations (4), (5), and (8), respectively. The ratio of the minimum of the lumen boundary radii to the maximum of the lumen boundary radii (LMMDev), the ratio of the minimum of the lumen boundary radii to the mean of the lumen boundary radii (LMinDev), the ratio of the mean of the lumen boundary radii to the maximum of the lumen boundary radii (LMaxDev), and the ratio of the standard deviation of the lumen boundary radii to the mean of the lumen boundary radii (LMeanDev) are calculated from:

$$\text{LMMDev} = (1.0 - \text{Min}L\text{Radii}/\text{Max}L\text{Radii}) \ast 100\% \quad (18)$$

$$\text{LMinDev} = (1.0 - \text{Min}L\text{Radii}/\text{Mean}L\text{Radii}) \ast 100\% \quad (19)$$

$$L\text{MaxDev}=(1.0-\text{Mean}L\text{Radii}/\text{Max}L\text{Radii})*100\% \quad (20)$$

$$L\text{MeanDev}=(SDL\text{Radii}/\text{Mean}L\text{Radii})*100\% \quad (21)$$

The mean of the outer-wall boundary radii (MeanWRadii), the minimum of the outer-wall boundary radii (MinWRadii), and the maximum of the outer-wall boundary radii (MaxWRadii) are computed using Equations (4), (5), and (8), respectively. The ratio of the minimum of the outer-wall boundary radii to the maximum of the outer-wall boundary radii (WMMDev), the ratio of the minimum of the outer-wall boundary radii to the mean of the outer-wall boundary radii (WMinDev), the ratio of the mean of the outer-wall boundary radii to the maximum of the outer-wall boundary radii (WMaxDev), and the ratio of the standard deviation of the outer-wall boundary radii to the mean of the outer-wall boundary radii (WMeanDev) are calculated as follows:

$$W\!M\!M\text{Dev}=(1.0-\text{Min}W\text{Radii}/\text{Max}W\text{Radii})*100\% \quad (22)$$

$$W\text{MinDev}=(1.0-\text{Min}W\text{Radii}/\text{Mean}W\text{Radii})*100\% \quad (23)$$

$$W\text{MaxDev}=(1.0-\text{Mean}W\text{Radii}/\text{Max}W\text{Radii})*100\% \quad (24)$$

$$W\text{MeanDev}=(SDW\text{Radii}/\text{Mean}W\text{Radii})*100\% \quad (25)$$

The mean of all wall thicknesses (MeanThick), the minimum of all wall thicknesses (MinThick), and the maximum of all wall thicknesses (MaxThick) are computed using Equations (10), (11), and (12), respectively. The ratio of the minimum of all wall thickness to the maximum of all wall thicknesses (TMMDev), the ratio of the minimum of all wall thicknesses to the mean of all wall thicknesses (TMinDev), the ratio of the mean of all wall thickness radii to the maximum of all wall thicknesses (TMaxDev), and the ratio of the standard deviation of all wall thicknesses to the mean of all wall thicknesses (TMeanDev) are determined as follows:

$$T\!M\!M\text{Dev}=(1.0-\text{MinThick}/\text{MaxThick})*100\% \quad (26)$$

$$T\text{MinDev}=(1.0-\text{MinThick}/\text{MeanThick})*100\% \quad (27)$$

$$T\text{MaxDev}=(1.0-\text{MeanThick}/\text{MaxThick})*100\% \quad (28)$$

$$T\text{MeanDev}=(SD\text{Thick}/\text{MeanThick})*100\% \quad (29)$$

The complexity descriptors characterize the relationship between two dimensional distances, i.e., lumen radii to outer boundary radii, or wall thickness to outer boundary radii. The complexity descriptors include lumen-wall descriptors, and thick-wall descriptors, which show relative variance between lumen boundary shape to outer wall boundary shape, and wall thickness shape to wall boundary shape. As noted above, FIGS. 7A-7D schematically illustrate such variances.

Complexity lumen-wall descriptors include the ratio of the minimum of the lumen radii to the mean of all wall radii (MinLW), the ratio of the maximum of the lumen radii to the mean of all wall radii (MaxLW), the ratio of the mean of the lumen radii to the mean of all wall radii (MeanLW), and the ratio of the distance between the lumen centroid and the outer-wall boundary centroid to the mean of all wall radii (EccentricityW). The EccentricityW demonstrates the level of relative variance of the eccentric distance between the lumen boundary and the outer-wall boundary to the mean of wall radii. MinLW, MaxLW, MeanLW and EccentricityW are determined as follows:

$$\text{Min}LW=(\text{Min}L\text{Radii}/\text{Mean}W\text{Radii})*100\% \quad (30)$$

$$\text{Max}LW=(\text{Max}L\text{Radii}/\text{Mean}W\text{Radii})*100\% \quad (31)$$

$$\text{Mean}LW=(\text{Mean}L\text{Radii}/\text{Mean}W\text{Radii})*100\% \quad (32)$$

$$\text{Eccentricity}W=(\text{Dist}/\text{Mean}W\text{Radii})*100\% \quad (33)$$

where $$\text{Dist}=\text{sqrt}((x_W-x_L)^2 * p_x^2 + (y_W-y_L)^2 * p_y^2) \quad (34)$$

and $(x_L, y_L)$, $(x_W, y_W)$ are respectively the lumen centroid and the outer-wall boundary centroid, and $p_x$, $p_y$ are the pixel size.

Complexity Thick-wall descriptors include the ratio of the minimum of all wall thicknesses to the mean of all wall radii (MinTW), the ratio of the maximum of all wall thicknesses to the mean of all wall radii (MaxTW), and the ratio of the mean of all wall thicknesses to the mean of all wall radii (MeanTW), calculated as follows:

$$\text{Min}TW=(\text{MinThick}/\text{Mean}W\text{Radii})*100\% \quad (35)$$

$$\text{Max}TW=(\text{MaxThick}/\text{Mean}W\text{Radii})*100\% \quad (36)$$

$$\text{Mean}TW=(\text{MeanThick}/\text{Mean}W\text{Radii})*100\% \quad (37)$$

To assess the reproducibility of the morphological descriptors described above, two experiments were designed to apply the morphological descriptors to data obtained from images of a carotid artery. In a first experiment, a volunteer traveled to three different facilities (the University of Washington Medical Center, the University of Utah Medical Center, and the Mayo Clinic), and the volunteer's carotid artery was scanned with a flow suppressed fast spin sequence at each facility. While each facility employed different imaging software, the scanners employed at each facility were identical, and the same imaging parameters were employed at each facility (image size=512×512/pixel size=0.32 mm/slice thickness=2.0 mm/number of slices=9). The resulting image data from each facility were reviewed by one expert. In a second experiment, two independent MR scans were taken within two weeks for each of fifteen patients distributed across two different facilities (the University of Washington Medical center and the Veteran's Affairs Puget Sound Health Care System). Each of the two MR scans for the same patient were performed by the same facility. Each facility employed the same imaging parameters (image size=512×512 pixels, pixel size=0.25 mm, slice thickness=2.0 mm, and number of slices=10). The fifteen patients ranged in age from 42 to 69 years. All protocols and consent forms were approved by each facilities' review board. In each patient, at least one side of the carotid stenosis was over 50% and less than 80%, as determined by duplex ultrasound examination. Two scans of fifteen patients ought to have yielded thirty carotid artery images for analysis; however, locational mismatching and poor image quality (caused by patient movement during scanning) resulted in only 24 useful carotid artery images being available for analysis. Two radiologists independently traced each patient's lumen and outer-wall boundaries using the semi-automatic Snake algorithm. Using the lumen and outer wall boundaries thus obtained, and wall thicknesses obtained as described above (i.e., using a combination of Delaunay triangulation and multiresolution tiling), the value of each of the 32 morphological descriptors noted above were automatically calculated. The bifurcation of the carotid artery was used as a reference point to match the carotid physical location so that the reproducibility of the results could be determined.

The reproducibility of the morphological descriptors were evaluated using pooled relative standard deviation (PRSD). The PRSD for a sample is calculated as follows:

$$PRSD = \sqrt{\frac{\sum_{p=1}^{l} \sum_{j=1}^{m} RSD_{p,j}^2}{l \cdot m}} \cdot 100\% \quad (38)$$

where $$RSD_{p,j} = \frac{\sqrt{\frac{\sum_{i=1}^{n} (x_{p,j,i} - \bar{x}_{p,j})^2}{n-1}}}{\bar{x}_{p,j}} \quad (39a)$$

or $$RSD_{p,j} = \sqrt{\frac{\sum_{i=1}^{n} (x_{p,j,i} - \bar{x}_{p,j})^2}{n-1}} \quad (39b)$$

$$\bar{x}_{p,j} = \frac{1}{n} \sum_{i=1}^{n} x_{p,j,i}$$

where $x_{p,j,i}$ is a morphological descriptor, $i=1, 2, \ldots, n$ is the index of a sample, $j=1, 2, \ldots, m$ is the slice index of carotid artery, and $p=1, 2, \ldots, l$ is the index of patient's carotid arteries. For the three sites experiment, $i=1, 2, 3, j=1, 2, \ldots, 9$, and $p=1$. For this experiment, $i=1, 2, j=1, 2, \ldots, 10$, and $p=1, 2, \ldots, 24$. Equation (39a) is used for descriptors that have a physical dimension, e.g., LumenArea, OuterArea. Equation (39b) is used for dimensionless descriptor, e.g., LORatio, LMMRadii. Equation (39b) expresses the standard deviation as a percentage of the maximum of the possible range of ratios, which is 1.0.

FIGS. 8A and 8B are visual representations of images obtained in the first experiment, where the carotid artery of one patient was imaged at three different facilities, and the images were reviewed by the same expert. FIGS. 8A and 8B show wall thickness in three slices around the bifurcation of the patient's left carotid artery. Images M-a1, M-a2, and M-a3 of FIGS. 8A and 8B were obtained at the Mayo Clinic, Images U-a1, U-a2, and U-a3 of FIGS. 8A and 8B were obtained at the University of Utah Medical Center, and Images W-a1, W-a2, and W-a3 of FIGS. 8A and 8B were obtained at the University of Washington Medical Center. In FIG. 8A, each image includes extracted contours, while in FIG. 8B, each image includes maximum and minimum thicknesses. Table 3 shows the pooled relative PRSD of the morphological descriptors of the patient's left carotid artery. The maximum PRSD among the descriptors is less than 7%. The results of this site-to-site study suggest that the morphological descriptors can be used to evaluate MR images obtained from different sites.

TABLE 3

PRSD of the descriptors: 1 volunteer imaged at 3 different facilities.

| Descriptors | PRSD | Mean | Descriptors | PRSD | Mean |
|---|---|---|---|---|---|
| LumenArea | 3.71% | 30.84 | WMinDev | 2.05% | 0.11 |
| OuterArea | 3.28% | 61.30 | WMaxDev | 1.73% | 0.08 |
| LORatio | 1.87% | 0.50 | Mean Thick | 5.53% | 1.27 |
| WallArea | 6.06% | 30.46 | Min Thick | 6.26% | 0.84 |
| MeanLRadii | 1.93% | 3.11 | Max Thick | 6.17% | 1.80 |

TABLE 3-continued

PRSD of the descriptors: 1 volunteer imaged at 3 different facilities.

| Descriptors | PRSD | Mean | Descriptors | PRSD | Mean |
|---|---|---|---|---|---|
| MinLRadii | 2.77% | 2.67 | TMMDev | 3.00% | 0.53 |
| MaxLRadii | 3.25% | 3.46 | TMeanDev | 2.95% | 0.19 |
| LMMDev | 3.07% | 0.20 | TMinDev | 2.13% | 0.34 |
| LMeanDev | 1.16% | 0.07 | TMaxDev | 3.93% | 0.29 |
| LMinDev | 2.31% | 0.13 | MinLW | 1.79% | 0.61 |
| LMaxDev | 1.63% | 0.09 | MaxLW | 2.29% | 0.78 |
| MeanWRadii | 1.58% | 4.40 | MeanLW | 1.37% | 0.70 |
| MinWRadii | 2.82% | 3.89 | MinTW | 1.06% | 0.19 |
| MaxWRadii | 2.32% | 4.85 | MaxTW | 2.39% | 0.41 |
| WMMDev | 2.74% | 0.18 | MeanTW | 1.38% | 0.29 |
| WMeanDev | 1.04% | 0.06 | EccentricityW | 1.30% | 0.05 |

FIGS. 9A and 9B are visual representations of images obtained in the first experiment, where the carotid arteries of 15 patients were imaged two different times over a two week period at the same facility, and the images were reviewed by different experts. FIGS. 9A and 9B do not show each image; instead, selected images from the experiment are provided. In FIG. 9A, each image includes extracted contours, while in FIG. 9B, each image includes an indication of maximum and minimum wall thicknesses. Table 4 shows the PRSD of the fifteen patients. The maximum PRSD among the descriptors is less than 12%. In Tables 3 and 4, descriptors involving outer wall measurements, such as wall area, tend to be less precise (expressing a relatively large PRSD), due to the greater difficulty in tracing outer wall boundaries. Ratios such as LORatio (lumen area/outer wall area) tend to be more precise (indicating a relatively smaller PRSD), because the ratios are in general small in magnitude, and therefore, the PRSD is small. The results of Tables 3 and 4 suggest that the morphological descriptors of the present invention can be used to monitor vascular plaque morphology progression and regression based on patient MR images.

TABLE 4

PRSD of the descriptors of fifteen patients (different analysts).

| Descriptors | PRSD | Mean | Descriptors | PRSD | Mean |
|---|---|---|---|---|---|
| LumenArea | 6.44% | 36.67 | WMinDev | 2.65% | 0.12 |
| OutArea | 5.85% | 85.75 | WMaxDev | 2.32% | 0.10 |
| LORatio | 3.02% | 0.42 | Mean Thick | 8.68% | 1.82 |
| WallArea | 10.19% | 49.09 | Min Thick | 11.55% | 0.98 |
| MeanLRadii | 3.23% | 3.32 | Max Thick | 11.18% | 2.90 |
| MinLRadii | 4.93% | 2.79 | TMMDev | 5.26% | 0.63 |
| MaxLRadii | 4.34% | 3.83 | TMeanDev | 4.26% | 0.27 |
| LMMDev | 3.85% | 0.26 | TMinDev | 5.58% | 0.44 |
| LMeanDev | 1.43% | 0.09 | TMaxDev | 4.68% | 0.35 |
| LMinDev | 3.08% | 0.16 | MinLW | 2.74% | 0.54 |
| LMaxDev | 2.27% | 0.12 | MaxLW | 3.32% | 0.73 |
| MeanWRadii | 2.87% | 5.17 | MeanLW | 2.40% | 0.64 |
| MinWRadii | 3.77% | 4.49 | MinTW | 2.06% | 0.19 |
| MaxWRadii | 4.32% | 5.81 | MaxTW | 5.87% | 0.56 |

TABLE 4-continued

PRSD of the descriptors of fifteen patients (different analysts).

| Descriptors | PRSD | Mean | Descriptors | PRSD | Mean |
| --- | --- | --- | --- | --- | --- |
| WMMDev | 3.87% | 0.21 | MeanTW | 2.42% | 0.36 |
| WMeanDev | 1.40% | 0.07 | EccentricityW | 3.46% | 0.11 |

Descriptor Legend
1. LumenArea: The area of the lumen.
2. OuterArea: The area of the outer-wall boundary.
3. WallArea: The area of the wall between the lumen boundary and the outer wall boundary.
4. LORatio: The ratio of the lumen area to the outer-wall boundary area.
5. MeanLRadii: The mean of the lumen boundary radii.
6. MinLRadii: The minimum of the lumen boundary radii.
7. MaxLRadii: The maximum of the lumen boundary radii.
8. LMMDev: The ratio of the minimum of the lumen boundary radii to the maximum of the lumen boundary radii.
9. LMinDev: The ratio of the minimum of the lumen boundary radii to the mean of the lumen boundary radii.
10. LMaxDev: The ratio of the mean of the lumen boundary radii to the maximum of the lumen boundary radii.
11. LMeanDev: The ratio of the standard deviation of the lumen boundary radii to the mean of the lumen boundary radii.
12. MeanWRadii: The mean of the outer-wall boundary radii.
13. MinWRadii: The minimum of the outer-wall boundary radii.
14. MaxWRadii: The maximum of the outer-wall boundary radii.
15. WMMDev: The ratio of the minimum of the outer-wall boundary radii to the maximum of the outer-wall boundary radii.
16. WMinDev: The ratio of the minimum of the outer-wall boundary radii to the mean of the outer-wall boundary radii.
17. WMaxDev: The ratio of the mean of the outer-wall boundary radii to the maximum of the outer-wall boundary radii.
18. WMeanDev: The ratio of the standard deviation of the outer-wall boundary radii to the mean of the outer-wall boundary radii.
19. MeanThick: The mean of all wall thicknesses.
20. MinThick: The minimum of all wall thicknesses.
21. MaxThick: The maximum of all wall thicknesses.
22. TMMDev: The ratio of the minimum of all wall thicknesses to the maximum of all wall thicknesses.
23. TMinDev: the ratio of the minimum of all wall thicknesses to the mean of all wall thickness.
24. TMaxDev: The ratio of the mean of all wall thicknesses to the maximum of all wall thicknesses.
25. TMeanDev: The ratio of the standard deviation of all wall thicknesses to the mean of all wall thicknesses.
26. MinLW: The ratio of the minimum of the lumen radii to the mean of all wall radii.
27. MaxLW: The ratio of the maximum of the lumen radii to the mean of all wall radii.
28. MeanLW: The ratio of the mean of the lumen radii to the mean of all wall radii.
29. EccentricityW: The ratio of the distance between the lumen centroid and the outer-wall boundary centroid to the mean of all wall radii.
30. MinTW: The ratio of the minimum of all wall thicknesses to the mean of all wall radii.
31. MaxTW: The ratio of the maximum of all wall thicknesses to the mean of all wall radii.
32. MeanTW: The ratio of the mean of all wall thicknesses to the mean of all wall radii.

The set of vascular morphological descriptors discussed above can be used to analyze vascular morphology. While the use of all of the descriptors defined above is preferred, it should be understood that the present invention is not limited to the use of the full set of descriptors defined above, as fewer than the thirty two descriptors defined above can be used to analyze plaque morphology. Preferably, at least two descriptors will be employed. The descriptors are defined based on lumen boundary, outer-wall boundary, and wall thickness. Prior art techniques are employed to define the lumen boundary and outer-wall boundary (i.e., the extracted contours of FIGS. 8A and 9A). Wall thickness is calculated using Delaunay triangulation and multiresolution tiling, as discussed above. The set of vascular morphological descriptors are calculated using the lumen boundary, the outer-wall boundary, and wall thickness values. The descriptors quantify the morphological size of the lumen, the outer-wall, and wall thickness, as well as their relative variant relationship. Empirical testing indicates the maximum PRSD among the descriptors is less than 7%. The descriptors show high reproducibility, with descriptors involving outer wall measurements showing the greatest variation.

In a preferred implementation, wall thickness calculations and the set of vascular morphological descriptors are automatically generated using a computing device. Such a computing device can be included in an imaging system used to collect the images, or the computing device can process stored images that are separately collected, perhaps at a previous time. The computing device can be configured to provide visual results, such as illustrated in the examples of FIGS. 8B and 9B, where minimum and maximum wall thicknesses are represented visually (the bright lines). The computing device can also be configured to provide numerical data relating to wall thicknesses, as well as the PRSD data provided in the examples shown in Tables 3 and 4. The computing device can be further configured to use the set of vascular morphological descriptors for clinical plaque analysis, producing results that quantitatively predict risk factors based on plaque morphology.

System for Implementing the Present Invention

FIG. 10 and the following related discussion are intended to provide a brief, general description of a suitable computing environment for practicing the present invention. As indicated above, the method of estimating wall thickness and the morphological descriptors can be used to automate analysis of plaque morphology. Thus one aspect of the present invention is an automated system to generate lumen image data (particularly image data corresponding to vascular structures) and to evaluate such image data. The processing can be implemented on a personal computer or other computing device. Those skilled in the art will appreciate that the present invention may be practiced with other computing devices, including a laptop and other portable computers, multiprocessor systems, networked computers, mainframe computers, and on other types of computing devices that include a processor, a memory, and optionally, a display.

The system of FIG. 10 includes a generally conventional imaging apparatus 30 (preferably an MRI system) that is controlled by a computer 32. Computer 32 may be a generally conventional personal computer (PC) or a dedicated controller specifically intended for controlling imaging apparatus 30. Although not specifically shown, when imaging apparatus 30 is implemented using an MRI system, imaging apparatus 30 will include a magnet to create a permanent magnetic field, a plurality of gradient coils to produce spatial variations of magnetic field, and an RF transceiver and receiver systems to transmit and receive RF signals to and from a plurality of RF coils, in the manner well known to those of ordinary skill in the art of MRI. Accordingly, details of the MRI apparatus, or other well known imaging apparatus that might be used in connection with the present invention, need not be specifically illustrated or discussed herein.

Computer 32 is coupled to a display 34, which is used for displaying images of slices to an operator. Included within computer 32 is a processor 36. A memory 38 (with both read only memory (ROM) and random access memory (RAM)), a storage 40 (such as a hard drive or other non-volatile data storage device) for storage of data, digital signals, and software programs, an interface 44, and a compact disk (CD) drive 46 are coupled to processor 36 through a bus 42. CD drive 46 can read a CD 48 on which machine instructions are stored for implementing the present invention and other software modules and programs that may be run by computer 32. The machine instructions are loaded into memory 38 before being executed by processor 36 to carry out the steps of the present invention.

Operation of imaging apparatus 30 is controlled by computer 32 when processor 36 executes the machine instructions stored in memory 38. These machine instructions cause the processor to implement the wall thickness estimation process discussed above, and calculation of each of the 32 morphological descriptors discussed in detail above. As lumen and outer wall boundary data are required to calculate the morphological descriptors defined above, computer 32 preferably is configured to facilitate conventional contour mapping to obtain the required lumen and outer wall boundary data. The resulting data are optionally stored on storage 40 so that selected slices can be displayed on display 34, or are directly displayed.

With respect to imaging apparatus 30, it should be understood that data from such an imaging apparatus can be collected and then stored in digital form, for later analysis by computer 32. That digital data can then later be loaded into the RAM of computer 32 via a network connection or digital memory media. Thus, imaging apparatus 30 is not required to be functionally coupled to computer 32, although such a configuration is likely to be particularly preferred, because analysis of such data can then be carried out in real-time.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for estimating a thickness of a wall of a lumen from an image of the lumen, comprising the steps of:
   (a) in an image of the lumen, identifying an inner contour and an outer contour;
   (b) performing a low resolution triangulation function to define triangles between the inner contour and the outer contour;
   (c) adding additional triangles between the inner contour and the outer contour;
   (d) analyzing edges of the triangles that were defined and added using a minimal energy function to identify triangle edges that correspond to a width between the inner contour and the outer contour;
   (e) comparing triangle edges identified as corresponding to a width between the inner contour and the outer contour to identify a minimum width and a maximum width corresponding respectively to a minimum wall thickness and a maximum wall thickness of the lumen; and
   (f) having identified the minimum width and the maximum width, executing at least one step selected from the group consisting of the following steps:
      (i) storing indications of the minimum width and the maximum width such that the indications are available for later use by a user; and
      (ii) outputting indications of the minimum width and the maximum width to a user.

2. The method of claim 1, further comprising the steps of repeating steps (c) and (d) until a desired resolution is achieved, such that additional triangle edges identified as corresponding to a width between the inner contour and the outer contour are compared to identify the minimum and the maximum width.

3. The method of claim 1, wherein the step of performing the low resolution triangulation function comprises the steps of:
   (a) decomposing the inner contour into a low resolution inner contour set using wavelet analysis;
   (b) decomposing the outer contour into a low resolution outer contour set using wavelet analysis; and
   (c) computing tiling for the low resolution inner contour set and the low resolution outer contour set using greedy triangulation.

4. The method of claim 1, wherein the step of analyzing the edges of the triangles using the minimal energy function comprises the step of using a Delaunay triangulation MaxMin angle property to determine the minimal energy function.

5. The method of claim 4, wherein the step of analyzing edges of the triangles using the minimal energy function further comprises the step of performing an edge flipping operation on the edges of the triangles.

6. The method of claim 1, wherein the step of adding additional triangles between the inner contour and the outer contour comprises the steps of:
   (a) inserting additional vertices onto each of the inner contour and the outer contour, such that triangles defined between the inner contour and the outer contour are converted to quadrilaterals; and
   (b) constructing an edge from each inserted vertex on one of the inner contour and the outer contour to a corresponding quadrilateral vertex on the other of the inner contour and the outer contour, thereby converting each quadrilateral into a pair of triangles.

7. The method of claim 1, wherein steps (a)-(e) are at least partially executed automatically by a computing device.

8. The method of claim 1, further comprising the step of using the inner contour, the outer contour, the minimum width and the maximum width to calculate a plurality of morphological descriptors for the lumen.

9. The method of claim 8, wherein the step of using the inner contour, the outer contour, the minimum width and the maximum width to calculate a plurality of morphological descriptors comprises the step of calculating a plurality of area descriptors.

10. The method of claim 9, wherein the step of calculating a plurality of area descriptors comprises the steps of calculating at least two of the following:
    (a) an area of the lumen;
    (b) an outer wall boundary area of the lumen;
    (c) a wall area of the lumen; and
    (d) a ratio of the area of the lumen to the outer wall boundary area.

11. The method of claim 8, wherein the step of using the inner contour, the outer contour, the minimum width and the maximum width to calculate a plurality of morphological descriptors comprises the step of calculating a plurality of simple descriptors, each simple descriptor being based on a one dimensional distance determined for the lumen.

12. The method of claim 11, wherein the step of calculating a plurality of simple descriptors comprises the steps of calculating at least two of the following:
    (a) a mean of lumen boundary radii;
    (b) a minimum of the lumen boundary radii;
    (c) a maximum of the lumen boundary radii;
    (d) a ratio of the minimum of the lumen boundary radii to the maximum of the lumen boundary radii;

19

(e) a ratio of the minimum of the lumen boundary radii to the mean of the lumen boundary radii;
(f) a ratio of the mean of the lumen boundary radii to the maximum of the lumen boundary radii; and
(g) a ratio of a standard deviation of the lumen boundary radii to the mean of the lumen boundary radii.

13. The method of claim 11, wherein the step of calculating a plurality of simple descriptors comprises the steps of calculating at least two of the following:
(a) a mean of outer wall boundary radii;
(b) a minimum of the outer wall boundary radii;
(c) a maximum of the outer wall boundary radii;
(d) a ratio of the minimum of the outer wall boundary radii to the maximum of the outer wall boundary radii;
(e) a ratio of the minimum of the outer wall boundary radii to the mean of the outer wall boundary radii;
(f) a ratio of the mean of the outer wall boundary radii to the maximum of the outer wall boundary radii; and
(g) a ratio of a standard deviation of the outer wall boundary radii to the mean of the outer wall boundary radii.

14. The method of claim 11, wherein the step of calculating a plurality of simple descriptors comprises the steps of calculating at least two of the following:
(a) a mean of all wall thicknesses of the lumen that were determined;
(b) a ratio of the minimum wall thickness to the maximum wall thickness;
(c) a ratio of the minimum wall thickness to the mean of all wall thicknesses;
(d) a ratio of the mean of all wall thicknesses to the maximum wall thickness; and
(e) a ratio of a standard deviation of all wall thicknesses to the mean of all wall thicknesses.

15. The method of claim 8, wherein the step of using the inner contour, the outer contour, the minimum width and the maximum width to calculate the plurality of morphological descriptors comprises the step of calculating a plurality of complexity descriptors, each complexity descriptor being based on two different dimensional distances determined for the lumen.

16. The method of claim 15, wherein the step of calculating a plurality of complexity descriptors comprises the steps of calculating at least two of the following:
(a) a ratio of a minimum of lumen radii to a mean of wall radii for the lumen;
(b) a ratio of a maximum of lumen radii to the mean of the wall radii;
(c) a ratio of a mean of the lumen radii to the mean of the wall radii; and
(d) a ratio of a distance between a centroid of the lumen and a centroid of the outer wall boundary to the mean of the wall radii.

17. The method of claim 15, wherein the step of calculating a plurality of complexity descriptors comprises the steps of calculating at least two of the following:
(a) a ratio of the minimum wall thickness to a mean of wall radii;
(b) a ratio of the maximum wall thickness to the mean of the wall radii; and
(c) a ratio of the mean of all wall thicknesses to the mean of the wall radii.

18. The method of claim 8, wherein the step of using the inner contour, the outer contour, the minimum width and the maximum width to calculate a plurality of morphological descriptors for the lumen comprises the step of calculating:

20

(a) a plurality of area descriptors;
(b) a plurality of simple descriptors, each simple descriptor being based on a one dimensional distance determined for the lumen; and
(c) a plurality of complexity descriptors, each complexity descriptor being based on two different dimensional distances determined for the lumen.

19. The method of claim 18, wherein each morphological descriptor is automatically calculated by a computing device.

20. The method of claim 18, wherein the lumen is a blood vessel of a patient, further comprising the step of analyzing the plurality of morphological descriptors to evaluate whether the patient is at risk for having a stroke.

21. A memory medium on which machine executable instructions are stored for carrying out the steps of claim 1.

22. A method for estimating a thickness of a wall of a lumen, comprising the steps of:
(a) identifying an inner contour and an outer contour of the lumen;
(b) generating a plurality of edges between the inner contour and the outer contour using multiresolution tiling;
(c) analyzing the plurality of edges using a Delaunay triangulation minimal energy function to identify edges that correspond to a width between the inner contour and the outer contour;
(d) comparing edges identified as corresponding to a width between the inner contour and the outer contour to identify a minimum width and a maximum width; and
(e) having identified the minimum width and the maximum width, executing at least one step selected from the group consisting of the following steps:
(i) storing indications of the minimum width and the maximum width such that the indications are available for later use by a user; and
(ii) outputting indications of the minimum width and the maximum width to a user.

23. The method of claim 22, further comprising the step of using the inner contour, the outer contour, the minimum width and the maximum width to calculate a plurality of morphological descriptors for the lumen.

24. The method of claim 23, wherein the step of using the inner contour, the outer contour, the minimum width and the maximum width to calculate a plurality of morphological descriptors comprises the step of calculating:
(a) a plurality of area descriptors;
(b) a plurality of simple descriptors, each simple descriptor being based on a one dimensional distance determined for the lumen; and
(c) a plurality of complexity descriptors, each complexity descriptor being based on two different dimensional distances determined for the lumen.

25. A memory medium on which machine executable instructions are stored for carrying out the steps of claim 22.

26. A method for estimating a thickness of a wall of a lumen, comprising the steps of:
(a) identifying an inner contour and an outer contour of a lumen;
(b) decomposing each of the inner contour and outer contour into a low resolution set of discrete points for the inner contour and a low resolution set of discrete points for the outer contour;
(c) employing a triangulation function to define triangles between the discrete points in each low resolution set;

(d) adding additional triangles between the inner contour and the outer contour;
(e) analyzing edges of the triangles that were defined and added to identify triangle edges that correspond to a width between the inner contour and the outer contour;
(f) comparing the triangle edges to identify a minimum width and a maximum width; and
(g) having identified the minimum width and the maximum width, executing at least one step selected from the group consisting of the following steps:
  (i) storing indications of the minimum width and the maximum width such that the indications are available for later use by a user; and
  (ii) outputting indications of the minimum width and the maximum width to a user.

27. The method of claim 26, wherein the step of adding additional triangles between the inner contour and the outer contour comprises the steps of:
  (a) inserting additional points onto each of the inner contour and the outer contour, such that triangles defined between the inner contour and the outer contour are converted to quadrilaterals; and
  (b) constructing an edge from each point that was inserted to a corresponding quadrilateral vertex on the other contour, thereby converting each quadrilateral into a pair of triangles.

28. The method of claim 26, wherein the step of analyzing triangle edges comprises the step of using a Delaunay triangulation MaxMin angle property to determine a minimal energy function.

29. The method of claim 26, further comprising the steps of repeating steps (e) and (f) until a desired resolution is achieved, such that additional triangle edges identified as corresponding to the width between the inner contour and the outer contour are compared to identify the minimum width and the maximum width.

30. The method of claim 26, further comprising the step of using the inner contour, the outer contour, the minimum width and the maximum width to calculate a plurality of morphological descriptors for the lumen.

31. A memory medium on which machine executable instructions are stored for carrying out the steps of claim 26.

32. A method for estimating a thickness of a wall of a lumen, comprising the steps of:
  (a) identifying an inner contour and an outer contour of the lumen;
  (b) decomposing the inner contour and the outer contour into a set of low resolution contours, to produce a pair of low resolution contour sets;
  (c) computing tiling to generate triangles for each low resolution contour set in which each triangle includes at least one cross edge extending between the inner contour and the outer contour;
  (d) labeling each cross edge as a suspect edge;
  (e) edge flipping each triangle relative to a cross edge thereof using a minimal energy function to identify cross edges that correspond to the width between the inner contour and the outer contour;
  (h) inserting a new vertex into each low resolution contour set, such that triangles defined by the pair of low resolution contour sets are converted to quadrilaterals;
  (g) constructing an edge from each inserted vertex in one of the low resolution sets of the pair to a corresponding quadrilateral vertex in the other low resolution contour set of the pair, to convert each quadrilateral into a pair of triangles;
  (h) labeling each cross edge as a suspect edge;
  (i) edge flipping each triangle relative to a cross edge thereof using the minimal energy function, to identify cross edges that correspond to the width between the inner contour and the outer contour;
  (j) repeating steps (f)-(i) until a desired resolution is achieved;
  (k) comparing cross edges identified as corresponding to the width between the inner contour and the outer contour to identify a minimum width and a maximum width; and
  (l) having identified the minimum width and the maximum width, executing at least one step selected from the group consisting of the following steps:
    (i) storing indications of the minimum width and the maximum width such that the indications are available for later use by a user; and
    (ii) outputting indications of the minimum width and the maximum width to a user.

33. The method of claim 32, further comprising the step of using the inner contour, the outer contour, the minimum width and the maximum width to calculate a plurality of morphological descriptors for the lumen.

34. A memory medium on which machine executable instructions are stored for carrying out the steps of claim 32.

35. A system for analyzing a lumen to determine dimensions of the lumen, including wall thickness, comprising:
  (a) imaging apparatus that produce an image of a lumen within a body of a patient; and
  (b) a computing device coupled to the imaging apparatus to control it, said computing device including:
    (i) a memory in which machine instructions are stored; and
    (ii) a processor coupled to the memory, said processor executing the machine instructions to control the imaging apparatus to carry out a plurality of operations, including:
      (1) identifying an inner contour and an outer contour of the lumen;
      (2) generating a plurality of edges between the inner contour and the outer contour using multiresolution tiling;
      (3) analyzing the plurality of edges using a Delaunay triangulation minimal energy fUnction to identify edges that correspond to a width between the inner contour and the outer contour;
      (4) comparing edges identified as corresponding to a width between the inner contour and the outer contour to identify a minimum width and a maximum width between the inner contour and the outer contour, corresponding respectively to a minimum wall thickness and a maximum wall thickness of the lumen; and
      (5) having identified the minimum width and the maximum width, executing at least one step selected from the group consisting of the following steps:
        (i) storing indications of the minimum width and the maximum width such that the indications are available for later use by a user; and
        (ii) outputting indications of the minimum width and the maximum width to a user.

36. The system of claim 35, further comprising a display coupled to the processor, wherein the machine instructions further cause the processor to display a discrete image of a selected slice of the lumen.

37. The system of claim 35, wherein the machine instructions further cause the processor to calculate a plurality of morphological descriptors for the lumen, the morphological descriptors including:
(a) a plurality of area descriptors;
(b) a plurality of simple descriptors, each simple descriptor being based on a one dimensional distance determined for the lumen; and
(c) a plurality of complexity descriptors, each complexity descriptor being based on two different dimensional distances associated with the lumen.

38. A system for analyzing a lumen to determine dimensions of the lumen, including wall thickness, comprising:
(a) a computer configured to process an image of a lumen, said computer including:
  (i) a memory in which machine instructions are stored;
  (ii) a display configured to display an image of a lumen; and
  (iii) a processor coupled to the memory and the display, said processor executing the machine instructions to carry out a plurality of operations, including:
    (1) in an image of the lumen, identifying an inner contour and an outer contour;
    (2) performing a low resolution triangulation function to define triangles between the inner contour and the outer contour;
    (3) adding additional triangles between the inner contour and the outer contour;
    (4) analyzing edges of the triangles that were defined and added using a minimal energy function to identify triangle edges that correspond to a width between the inner contour and the outer contour;
    (5) comparing triangle edges identified as corresponding to a width between the inner contour and the outer contour to identify a minimum width and a maximum width corresponding respectively to a minimum wall thickness and a maximum wall thickness of the lumen; and
    (6) having identified the minimum width and the maximum width, executing at least one step selected from the group consisting of the following steps:
      (i) storing indications of the minimum width and the maximum width such that the indications are available for later use by a user; and
      (ii) outputting indications of the minimum width and the maximum width to a user.

39. The system of claim 38, wherein the machine instructions further cause the processor to iteratively add additional triangles between the inner contour and the outer contour until a predetermined resolution is achieved.

40. The system of claim 38, wherein the machine instructions further cause the processor to perform the low resolution triangulation function by implementing the following operations:
(a) decomposing the inner contour into a low resolution inner contour set using wavelet analysis, and decomposing the outer contour into a low resolution outer contour set using wavelet analysis; and
(b) computing tiling for the low resolution inner contour set and the low resolution outer contour set using greedy triangulation.

41. The system of claim 38, wherein the machine instructions further cause the processor to analyze the edges of the triangles using a Delaunay triangulation MaxMin angle property to determine the minimal energy function.

42. The system of claim 38, wherein the machine instructions further cause the processor to analyze triangle edges by performing an edge flipping operation on the edges of the triangles.

43. The system of claim 38, wherein the machine instructions further cause the processor to add additional triangles between the inner contour and the outer contour by implementing the following operations:
(a) inserting vertices onto each of the inner contour and the outer contour, such that triangles defined between the inner contour and the outer contour are converted to quadrilaterals; and
(b) constructing an edge from each inserted vertex on one of the inner contour and the outer contour to a corresponding quadrilateral vertex on the other of the inner contour and the outer contour, thereby converting each quadrilateral into a pair of triangles.

44. The system of claim 38, wherein the machine instructions further cause the processor to calculate a plurality of morphological descriptors for the lumen, the morphological descriptors including:
(a) a plurality of area descriptors;
(b) a plurality of simple descriptors, each simple descriptor being based on a one dimensional distance determined for the lumen; and
(c) a plurality of complexity descriptors, each complexity descriptor being based on two different dimensional distances determined for the lumen.

\* \* \* \* \*

UNITED STATES PATENT AND TRADEMARK OFFICE
CERTIFICATE OF CORRECTION

PATENT NO. : 7,353,117 B2
APPLICATION NO. : 10/804460
DATED : April 1, 2008
INVENTOR(S) : Yuan et al.

Page 1 of 1

It is certified that error appears in the above-identified patent and that said Letters Patent is hereby corrected as shown below:

| | |
|---|---|
| Column 1, line 11 | The paragraph under the heading "Government Rights" should be deleted and replaced in its entirety with the following: --This invention was made with government support under contract number HL60213 and HL61851 awarded by the National Institutes of Health. The Government has certain rights in the invention.-- |
| Column 3, line 54 | after "change" delete "changes" |
| Column 7, line 52 | after "invention" delete "is" |
| Column 14, line 56 | "OutArea" should read --OuterArea-- |
| Column 16, line 52 | "systems" should read --system-- |
| Column 21, line 31 (Claim 29, line 1) | "fun her" should read --further-- |

Signed and Sealed this

Eighteenth Day of November, 2008

JON W. DUDAS
*Director of the United States Patent and Trademark Office*